US010586678B2

(12) United States Patent
Caspi et al.

(10) Patent No.: US 10,586,678 B2
(45) Date of Patent: Mar. 10, 2020

(54) LEFT-RIGHT CANTED-COSINE-THETA MAGNETS

(71) Applicant: The Regents of the University of California, Oakland, CA (US)

(72) Inventors: Shlomo Caspi, Alameda, CA (US); Lucas Brouwer, Berkeley, CA (US); Weishi Wan, Walnut Creek, CA (US); David Robin, Oakland, CA (US); Soren Prestemon, Martinez, CA (US)

(73) Assignee: The Regents of the University of California, Oakland, CA (US)

( * ) Notice: Subject to any disclaimer, the term of this patent is extended or adjusted under 35 U.S.C. 154(b) by 35 days.

(21) Appl. No.: 15/542,383

(22) PCT Filed: Jan. 8, 2016

(86) PCT No.: PCT/US2016/012612
§ 371 (c)(1),
(2) Date: Jul. 7, 2017

(87) PCT Pub. No.: WO2016/114989
PCT Pub. Date: Jul. 21, 2016

(65) Prior Publication Data
US 2017/0372867 A1    Dec. 28, 2017

Related U.S. Application Data

(60) Provisional application No. 62/220,185, filed on Sep. 17, 2015, provisional application No. 62/102,348, filed on Jan. 12, 2015.

(51) Int. Cl.
*H01J 37/147*    (2006.01)
*A61N 5/10*    (2006.01)
(Continued)

(52) U.S. Cl.
CPC .......... *H01J 37/1475* (2013.01); *A61N 5/10* (2013.01); *A61N 5/1081* (2013.01); *H01F 5/02* (2013.01);
(Continued)

(58) Field of Classification Search
CPC .................................................. H01J 37/1475
(Continued)

(56) References Cited

U.S. PATENT DOCUMENTS

| | | | | |
|---|---|---|---|---|
| 4,392,111 A * | 7/1983 | Rostoker | ............... | H05H 11/00 315/501 |
| 6,921,042 B1 * | 7/2005 | Goodzeit | ............... | H01F 7/202 242/430 |
| 2012/0065073 A1 * | 3/2012 | Maher | ............... | G01R 33/3815 505/162 |

* cited by examiner

*Primary Examiner* — Jason L McCormack
(74) *Attorney, Agent, or Firm* — Knobbe Martens Olson & Bear LLP

(57) ABSTRACT

Disclosed herein are superconducting gantry magnets that include multiple quadrupole winding sections placed in sequence on a curve such that the effective current direction is reversed between sections. This produces alternating quadrupole field regions along the length of the bend whose individual integral strengths can be tuned by the location of the current polarity transitions. A simple transition scheme to reverse the current between sections can be implemented to allow for the use of one continuous winding and power supply. Dipole windings can be included in the superconducting gantry magnets so that the magnets produce superposed dipole and alternating quadrupole fields. The disclosed design for the windings and transition scheme to reverse current polarity can be implemented for higher order multipoles as well.

9 Claims, 15 Drawing Sheets

(51) Int. Cl.
  *H01F 6/06* (2006.01)
  *H01F 5/02* (2006.01)
  *H01F 27/28* (2006.01)
  *H01F 41/04* (2006.01)
  *H05H 7/00* (2006.01)
  *H05H 7/04* (2006.01)

(52) U.S. Cl.
  CPC ............... *H01F 6/06* (2013.01); *H01F 27/28* (2013.01); *H01F 41/048* (2013.01); *A61N 2005/1087* (2013.01); *H05H 2007/002* (2013.01); *H05H 2007/048* (2013.01); *H05H 2277/11* (2013.01)

(58) Field of Classification Search
  USPC .................................................. 250/396 ML
  See application file for complete search history.

LEFT-RIGHT CANTED-COSINE-THETA MAGNETS

CROSS-REFERENCE TO RELATED APPLICATIONS

This claims priority to U.S. Prov. Pat. App'n No. 62/102,348, filed Jan. 12, 2015, entitled "Left-Right Canted-Cosine-Theta (CCT) Windings Configured to Generate Compact Alternating Multipole Coils," and to U.S. Prov. App'n No. 62/220,185, filed Sep. 17, 2015, entitled "Left-Right Canted-Cosine-Theta Magnets," the entire contents of each of which is incorporated by reference herein in its entirety.

STATEMENT REGARDING FEDERALLY SPONSORED R&D

The inventions described and claimed herein were made with government support under Contract No. DE-AC02-05CH11231 awarded by the U.S. Department of Energy. The government has certain rights in this invention.

BACKGROUND

Field

The disclosure generally relates to magnets for accelerator beamlines, and in particular to high-field, superconducting, bending magnets for accelerator beamlines.

Description of Related Art

State-of-the-art ion beam cancer therapy utilize rotatable accelerator beamlines, called gantries, that direct and scan an ion beam over tumors from multiple angles. This technique potentially gives the best possible dose distribution. In the scanning approach, the energy deposition is focused and controlled, allowing for greater accuracy in treatment and reduced collateral damage to healthy tissue. The depth of scanning can be adjusted by changing the beam energy, whereas the beam transverse position can be changed using fast sweeper magnets. These sweeper magnets can be located upstream and/or downstream of a final, resistive, bending magnet. The size and weight of these gantries can depend on the size and weight of the magnets in the system.

SUMMARY

Example embodiments described herein have innovative features, no single one of which is indispensable or solely responsible for their desirable attributes. Without limiting the scope of the claims, some of the advantageous features will now be summarized.

In a first aspect, a superconducting gantry magnet is provided, the magnet including a pair of quadrupole layers configured to provide an alternating quadrupole field in a bore of the superconducting gantry magnet. Each quadrupole layer includes a mandrel comprising ribs forming a helical conductor channel comprising an undulating canted pattern around a bore axis of the superconducting gantry magnet, a plurality of transition locations formed by the conductor channel configured to change a direction of the winding around the mandrel while maintaining the same undulating canted pattern, and a superconductor cable wound around the mandrel within the conductor channel. The magnet includes a pair of dipole layers configured to provide a dipole field in the bore of the superconducting gantry magnet. Each dipole layer includes a mandrel comprising ribs, the ribs forming a helical conductor channel comprising a canted pattern around a bore axis of the superconducting gantry magnet. The magnet includes a superconductor wire or cable wound around the mandrel within the conductor channel. The respective mandrels are configured to nest within one another around the bore axis.

In some embodiments of the first aspect, the magnet further includes a quadrupole power supply configured to provide electrical power to the superconductor wires or cables of the quadrupole layers and a dipole power supply configured to provide electrical power to the superconducting wires or cables of the dipole layers.

In some embodiments of the first aspect, the alternating quadrupole field is configured to alternate between focusing and de-focusing sections. In a further embodiment, the alternating quadrupole field includes at least three alternating sections. In another further embodiment, the alternating quadrupole field includes at least five alternating sections.

In some embodiments of the first aspect, the dipole field has a strength that is at least about 2 T and the quadrupole field has a strength that is at least about 20 T/m within the bore. In some embodiments of the first aspect, the superconducting gantry magnet is substantially achromatic over a range of energies of about ±20%. In some embodiments of the first aspect, the magnet includes a pair of sextupole layers configured to provide an alternating sextupole field in the bore of the superconducting gantry magnet, each sextupole layer comprising a mandrel comprising ribs, the ribs forming a helical conductor channel comprising an undulating canted pattern around a bore axis of the superconducting gantry magnet; a plurality of transition locations formed by the conductor channel configured to change a direction of the winding around the mandrel while maintaining the same undulating canted pattern; and a superconductor wire or cable wound around the mandrel within the conductor channel. In some embodiments of the first aspect, the respective mandrels form a portion of a torus.

In a second aspect, a method of manufacturing a superconducting gantry magnet is provided. The method includes manufacturing a plurality of identical annular laminations, each identical annular lamination having an integer multiple of a length of an axial period of a turn of a quadrupole layer, individual annular laminations having ribs and a spar that, when joined together, form a mandrel layer with a winding channel formed by the ribs. The method includes producing a plurality of lamination pieces each comprising ribs that, when joined with the identical annular laminations, form a mandrel layer with a turning location in the winding channel representing a conductor reversal. The method includes repeatedly joining together a subset of the identical annular laminations to form a plurality of mandrel sections, wherein individual identical annular laminations are aligned to form a continuous winding channel. The method includes joining a turning location lamination to individual formed mandrel sections, the turning location lamination aligned at an end of the formed mandrel section so that laminations form a continuous winding channel that changes direction in a winding direction at the turning location. The method includes forming a mandrel by joining the formed mandrel sections having the turning location laminations, wherein individual mandrel sections are aligned so that the sections with the turning location laminations form a continuous winding channel. The method includes winding a conductor around the mandrel so that at least a portion of the conductor is contained within the formed continuous winding channel.

In some embodiments of the second aspect, the conductor comprises at least one of single strand wires, multiple single strand insulated wires co-located in the channel and connected electrically in series, or with composite cables. In some embodiments of the second aspect, the mandrel composite cables comprise Rutherford cables. In some embodiments of the second aspect, the mandrel forms a 90 degree bend. In some embodiments of the second aspect, the individual laminations are joined using adhesives. In some embodiments of the second aspect, the turning location is configured to be at a pole of an undulating helical winding channel. In some embodiments of the second aspect, the ribs are configured to reduce stress accumulation between turns.

In some embodiments, a superconducting magnet is provided, the magnet having multiple layers, and individual layers are formed using the method of the second aspect.

In a third aspect, an isocentric gantry is provided that is configured to deliver particle radiation therapy to a patient. The gantry includes a plurality of superconducting gantry magnets, each magnet comprising nested dipole and quadrupole magnets configured to produce a dipole field and an alternating quadrupole field in a bore of the magnet, the magnets arranged in a particle beam line and configured to change a direction of the particle beam line. The alternating quadrupole field is provided by a pair of nested quadrupole layers, each layer comprising a winding of superconducting wire or cable around a mandrel that changes winding direction at a plurality of transition locations while maintaining a pattern of the winding.

In some embodiments of the third aspect, the isocentric gantry has a momentum acceptance ranging from approximately up to about ±20% without changing magnetic field of the plurality of superconducting gantry magnets. In some embodiments of the third aspect, the plurality of superconducting gantry magnets are configured to provide achromatic beam optics of the particle beam line. In some embodiments of the third aspect, the plurality of superconducting gantry magnets are configured to transmit the particle beam line whose energy is rapidly changed without changing a magnetic field strength. In some embodiments of the third aspect, the only quadrupole magnetic fields in the gantry are provided by the plurality of superconducting gantry magnets. In some embodiments of the third aspect, the dipole magnets of at least one superconducting gantry magnet are configured to produce an alternating dipole field in the bore of the magnet configured to provide alternating bend directions of the particle beam line with rapid transitions between bend directions, wherein the alternating dipole field is provided by a pair of nested dipole layers, each layer comprising a winding of superconducting wire or cable around a mandrel that changes winding direction at a plurality of transition locations while maintaining a pattern of the winding. In some embodiments of the third aspect, at least one superconducting gantry magnet comprises nested sextupole magnets configured to produce an changing sextupole field in the bore of the magnet configured to provide chromatic corrections in the particle beam line, wherein the changing sextupole field is provided by a pair of nested sextupole layers, each layer comprising a winding of superconducting wire or cable around a mandrel that changes winding direction at a plurality of transition locations while maintaining a pattern of the winding.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

DETAILED DESCRIPTION

Figure 1:
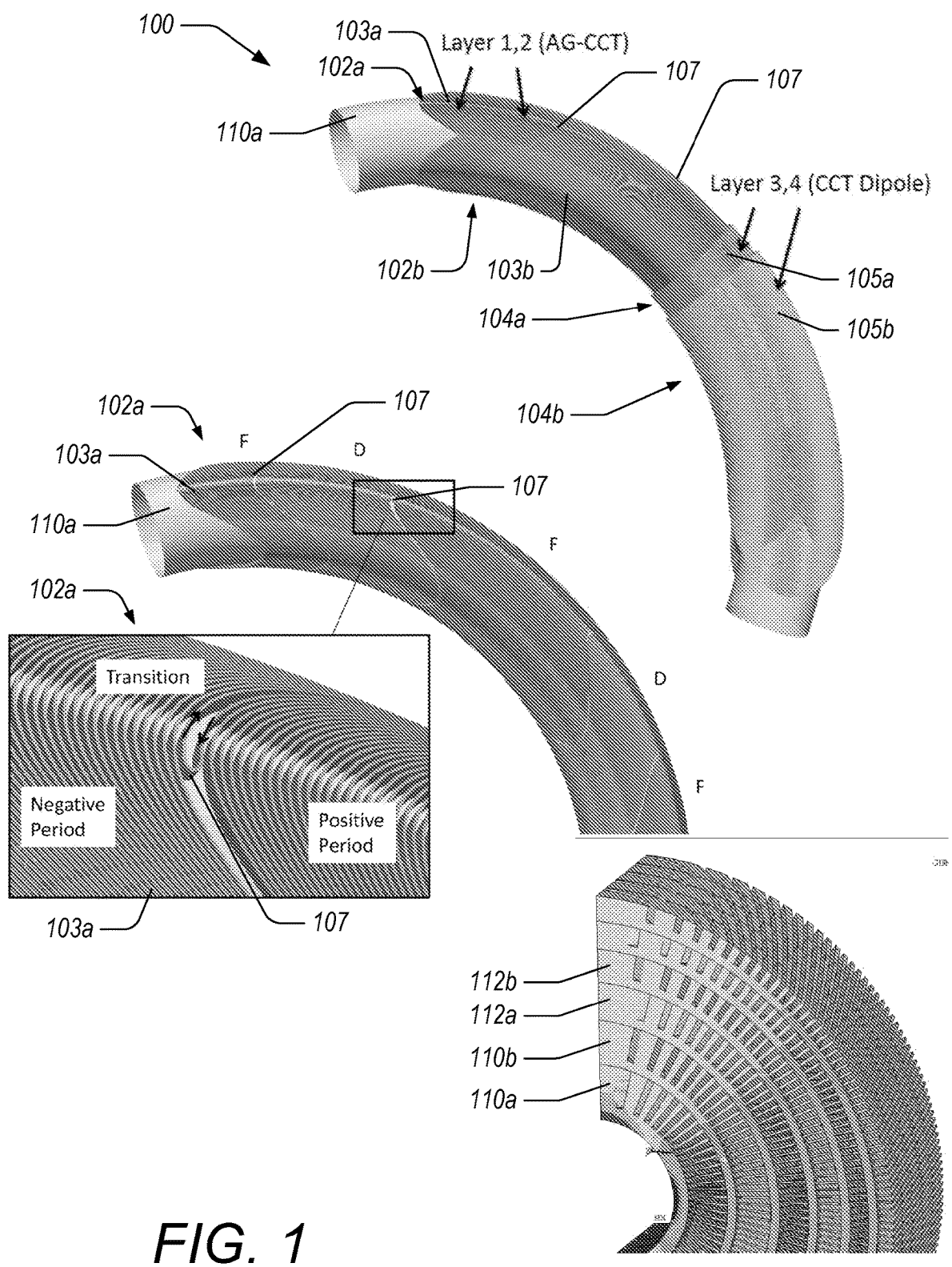
FIG. 1 illustrates an example superconducting gantry magnet. The magnet includes four winding layers.

Generally described, aspects of the present disclosure relate to superconducting magnets with a multi-layer design, the combined layers providing magnetic fields for steering and focusing a particle beam. The disclosed magnets can superpose magnetic fields of nested and tilted solenoids that are oppositely skewed or canted. The windings of some layers of the nested and tilted solenoids can switch direction to rapidly change the resulting magnetic field. This is generally referred to herein as a left-right design, or a design where the directions of the windings of conductors around a bore changes direction. When a left-right canted magnet design is applied to a quadrupole winding, this approach can yield an alternating gradient or alternating quadrupole field. The disclosed magnets can have a cross-sectional current density that behaves like a cosine function. For reference, in the limit that the current density behaves exactly as $\cos(n\theta)$, the resulting field approaches a perfect n multipole, where $n=1$ would be a pure dipole, $n=2$ would be a pure quadrupole, etc. The number of oscillations in the cosine function is related to the multipole magnetic field produced by the disclosed superconducting magnets. Accordingly, disclosed herein are superconducting magnets that can be referred to as left-right canted-cosine-theta magnets. These superconducting magnets can be configured to be achromatic over a relatively wide range of momentum and energy. Advantageously, gantries incorporating the disclosed superconducting magnets can be smaller in size and weight and can be less costly to manufacture than gantries incorporating other magnet designs.

Although examples and implementations described herein focus, for the purpose of illustration, on implementation in gantries for ion-based therapy, the systems and methods disclosed herein can be implemented in applications in accelerator and X-ray radiation source design, particle beam accelerators and storage rings, magneto hydrodynamic propulsion magnets for seagoing vessels, superconducting motor stators, rotors for an induction motor, or the like. Various aspects of the disclosure will now be described with regard to certain examples and embodiments, which are intended to illustrate but not limit the disclosure.

Making a compact and light-weight ion beam therapy gantry system is advantageous because it can reduce the cost of making such systems and can improve the quality of treatment provided by these systems. To make the system compact, superconducting magnets can be used that can achieve fields that exceed the capabilities of typical resistive magnets. Gantries with superconducting magnets may advantageously reduce the overall size, weight, and cost of the system.

Superconducting magnets, however, may be quenched if exposed to too much heat or if they generate too much heat. In some situations, quickly ramping the magnetic field of these magnets may generate heat that can quench the magnet. As described herein, it is generally desirable to be able to rapidly change the magnetic field in the gantry as the beam energy is changed to scan, for example, a tumor. In such a gantry, any limitation in the ramping speed potentially limits the performance of the system and time to carry out a treatment.

Accordingly, described herein is a compact superconducting magnet system that is compact, lightweight, and allows fast energy ramping without ramping the magnetic field quickly. The system includes beam optics that are achromatic that are configured to guide particles with a relatively wide range of energies along a targeted path without changing the magnetic field of the disclosed superconducting magnets. This is accomplished at least in part through the use of superconducting magnets that are configured to quickly switch the sign of a strong quadrupole along a beam path. As described in greater detail herein, the switch between signs of the quadrupole along the beam path can be accomplished by switching a direction of conductor windings around the magnet while maintaining the overall pattern of the winding. This technique may also be applied to different multipole magnets (e.g., sextupoles, octupoles, etc.).

The disclosed superconducting magnets can be used in gantries to reduce the size and weight of the gantries. These magnets can provide the desired bending and focusing properties of the gantry system using magnets that are smaller in size and weight and can reduce the overall cost of the system. These superconducting magnets can be used to create achromatic systems, increasing the beam energy acceptance relative to typical gantry systems incorporating resistive magnets. This can advantageously increase scanning speed, potentially allowing the introduction of new irradiation methods. Thus, the disclosed superconducting magnets can be used in gantry systems to provide fast scanning in direction and energy while reducing system weight.

The disclosed superconducting magnets can be configured to provide bending for particles with relatively high magnet rigidities. For example, typical ion beam energies can be about 250 MeV for protons and 400 MeV/nucleon for carbon and can have magnet rigidity of respectively about 2.2 Tm and about 6.6 Tm. The disclosed superconducting magnets can have a relatively large aperture (e.g., about 250 mm diameter aperture to allow for upstream scanning magnets).

The disclosed superconducting magnets can be used in a gantry system as the final bending magnet configured to be curved, to provide a relatively large magnetic field, to have a relatively large aperture, to provide superior field quality to allow for transverse scanning with little distortion, to be fully rotatable, and to be able to perform fast-field ramping for rapid energy scanning. The large energy acceptance magnets disclosed herein use quadrupole and higher order multipole magnetic components to allow for the large energy acceptance. The disclosed magnets can be an achromatic superconducting magnet design with beam optics tailored for a high performance superconducting gantry magnet system. The disclosed systems include achromatic, combined-function optics design that provides a large-energy acceptance, allowing fast depth-scanning while reducing the need for fast magnetic field ramping.

In some embodiments, the superconducting magnets can include a winding support structure that integrates conduction cooling while reducing eddy-currents associated with field ramping. In some embodiments, cooling of the superconducting magnets can be provided by cryocoolers. In some embodiments, the design and cooling of the superconducting magnets can be configured to reduce quenching of the superconducting magnets due at least in part to the reduction of AC- and eddy-current losses and/or to reducing the need to rapidly change the magnetic field of the superconducting magnets.

In some embodiments, an ion treatment gantry is provided that has a field size at target of about 25 cm, a source-to-axis distance (SAD) of greater than or equal to about 4 m, a relatively small spot size at isocenter (e.g., 2 s is between about 3 mm and about 6 mm), an achromatic field bending system configured to provide a large momentum acceptance (e.g., $\Delta p/p > \pm 10\%$, $-\Delta p/p/+\Delta p/p$ is about $-5\%/+20\%$, etc.), a final bend magnet with a dipole magnetic field greater than or equal to about 2 T and a quadrupole field of about 20 T/m quadrupole field with an alternating quadrupole along the beam path for the achromatic optics. The ion treatment gantry can be configured to provide depth scanning of up to about 10 cm without changing magnetic field in the superconducting magnets. Such a gantry can be configured to weigh less than about 9 tons with the incorporation of the disclosed superconducting magnets.

Herein disclosed are superconducting gantry magnets that include multiple quadrupole winding sections placed in sequence on a curve such that the effective current direction is reversed between sections. This produces alternating quadrupole field regions along the length of the bend whose individual integral strengths can be tuned by the location of the current polarity transitions. A simple transition scheme to reverse the current between sections can be implemented to allow for the use of one continuous winding and power supply. In this scheme the ends of each section nest inside the next section, resulting in an alternating focusing system that can be both compact and efficient.

The method for changing the current between sections makes use of the axial periodicity of windings of the magnet (e.g., a left- or right-handed "corkscrew" winding pattern). Changing the direction of this period (e.g., switching from left- to right-handed corkscrew), switches the azimuthal direction of the axial current and thus the transverse fields. After a winding path is tailored to produce a quadrupole, the coil can be split up into sections of alternating axial period based on the targeted integrated strengths of the focusing and defocusing regions. Once the coil sections are determined, only a short reverse bend is utilized to transition between regions and to maintain one continuous winding. The result is a highly efficient transition from focusing to defocusing quadrupoles.

In some embodiments, this same approach can be used for dipole windings to produce fields of opposite polarity with short transition lengths. Such fields may be of interest, for example, for "wavelength shifters", e.g., devices applied to charged particle beams (typically electrons) that produce intense, high photon-energy synchrotron radiation with no net beam steering or displacement.

Example Achromatic Superconducting Gantry Magnet

FIG. 1 illustrates an example superconducting gantry magnet 100. The magnet 100 includes four winding layers. The two inner layers 102a, 102b are configured to provide a quadrupole field and the two outer layers 104a, 104b are configured to provide a dipole field. The four winding layers comprise concentric pairs of oppositely-tilted, helically-wound coils connected in such a way that the solenoid field in each pair is canceled and the dipole fields and quadrupole fields add. Each layer can have its own support structure, a mandrel 110a, 110b, 112a, 112b, comprising a tube (e.g., a straight tube or a curved tube) with channels cut into it that guide a conductor around a bore.

In the magnet 100, each distinct pair of layers provides specific multipole contribution(s) (e.g., quadrupole layers 102a, 102b, dipole layers 104a, 104b, and this can be extended to other multipoles as described herein). Each pair of layers can be operated with its own power supply. The magnet 100 advantageously provides a highly-efficient means of alternating the quadrupole field, resulting in a field profile that approaches that of the ideal sharp cut-off model ("SCOFF" model), and that enhances the optical performance of the achromatic properties of a gantry system in which it may be utilized. In addition, the magnet 100 is configured to superimpose a bending magnet (e.g., the dipole layers 104a, 104b) on top of adjacent quadrupoles (e.g., the quadrupole layers 102a, 102b) wherein the quadrupole fields are configured to alternate the direction of the quadrupole field to strongly focus particles in the beam path in an achromatic fashion.

The outer layer 104a includes a helically wound right tilted coil 105a about an outer mandrel 110a. The outer layer 104b includes a helically wound left tilted coil 105b about an outer mandrel 110b. The outer mandrels 110a, 110b can be a coil form, a support tube, and the like. The coils 105a can be wound in a counter-clockwise direction when looking along the axis of the mandrels 110a, 110b from a first end with the windings being tilted at a first angle with respect to a central z-axis of the coils 105a, 105b. Similarly, the coils 105b can be wound in a clockwise direction when looking along the axis of the mandrels 110a, 110b from the first end with the windings being tilted at an angle opposite the first angle with respect to the central z-axis of the coils.

For example, the tilting of the respective coils 105a, 105b being configured to generate longitudinal magnetic fields within the bore of the mandrel 110 that cancel each other out while generating transverse fields that combine to provide a dipole field within the bore. This is accomplished due at least in part to the coil windings 105a, 105b being wound in opposite directions and being tilted opposite to each other. As a result, the current flows in opposite directions in the two coils 105a, 105b and each coil produces total field vectors that are generally perpendicular to the tilted planes of the coils 105a, 105b. The total field has a component along the bore axis (e.g., the z-direction) and a component perpendicular to the bore axis (e.g., in the x-y plane). The contributions to the magnetic field in the z-direction of the coils 105a, 105b are configured to act in opposite directions, effectively canceling one another, while the contributions to the magnetic field in the x-y plane are configured to act in the same direction.

The inner layer 102a includes an undulating, helically wound right tilted coil 103a about an inner mandrel 112a. The inner layer 102b includes an undulating, helically wound left tilted coil 103b about an inner mandrel 112b. The inner mandrels 112a, 112b can be a coil form, a support tube, and the like. The coils 103a can be wound in a counter-clockwise direction in a first portion and in a clockwise direction in a second portion when looking along the axis of the mandrels 112a, 112b from a first end. Similarly, the coils 103b can be wound in a clockwise direction in a first portion (configured to be positioned around the first portion of the coils 103a) and in a counter-clockwise direction in a second portion (configured to be positioned generally around the second portion of the coils 103b) when looking along the axis of the mandrels 110a, 110b from the first end. The respective windings of the inner layers 102a, 102b can be tilted at opposite angles with respect to the central z-axis of the coils 103a, 103b. The winding pattern of the coils 103a, 103b can remain substantially the same before and after the locations 107 where the windings change direction. These locations can include a transition 107 where the windings change direction around the mandrels 112a, 112b. By changing the direction of the windings, the direction of the resulting quadrupole field can change relatively quickly along the bore axis (e.g., changing from a focusing to a de-focusing field).

The two inner layers 102a, 102b can be configured to provide an alternating quadrupole field that acts to alternately focus and de-focus a particle beam (with respect to a first plane, the quadrupole field acts to alternately de-focus and focus the particle beam with respect to a second plane orthogonal to the first plane). In some embodiments, the superconducting gantry magnet 100 can include at least 3 alternating focus (F) and de-focus (D) portions (e.g., the superconducting gantry magnet can have an FDF structure). In some embodiments, the superconducting magnet 100 can include at least 5 alternating portions (e.g., FDFDF), at least 4 alternating portions, at least 6 alternating portions, at least 7 alternating portions, between 3 and 7 alternating portions, etc. In certain implementations, the inner layers 102a, 102b can provide a gradient magnetic field having a field strength of at least about 20 T/m.

Alternating focusing (F) and defocusing (D) quadrupole magnets may be used to guide and focus particle beams. With the superconducting gantry magnet 100, continuous, alternating windings can be made by reversing the winding direction from counter clockwise to clockwise while maintaining a forward pitch. The windings can be configured to maintain the same pattern over the coils, preserving the field quality over the alternating magnets including ends and transitions.

The transition location 107 represents a transition between focusing and de-focusing quadrupoles. The two quadrupole layers 102a, 102b can be implanted using curved, nested mandrels 112a, 112b. The winding channels in the defocusing quad turn counter-clockwise as the pitch goes forward, and those in the focusing quad reverse to a clock-wise direction but still maintain a forward pitch. To reverse the current, the respective quadrupoles include a transition location 107 (e.g., a 180 degree bend).

In certain implementations, the outer layers 104a, 104b can provide a dipole magnetic field having a field strength of at least about 2 T, at least about 3.5 T, etc. This can be configured to provide a bending radius of about 1.25 m for a proton with an energy of about 250 MeV. This can be configured to enable a relatively large field size at the isocenter (e.g., greater than about 25 cm), with relatively small non-linear distortions over the full field. The superconducting gantry magnet 100 can also be configured to provide a relatively large SAD (e.g., greater than about 4 m). The superconducting gantry magnet 100 can have a relatively large energy acceptance as well (e.g., greater than about ±20%).

Figure 2:
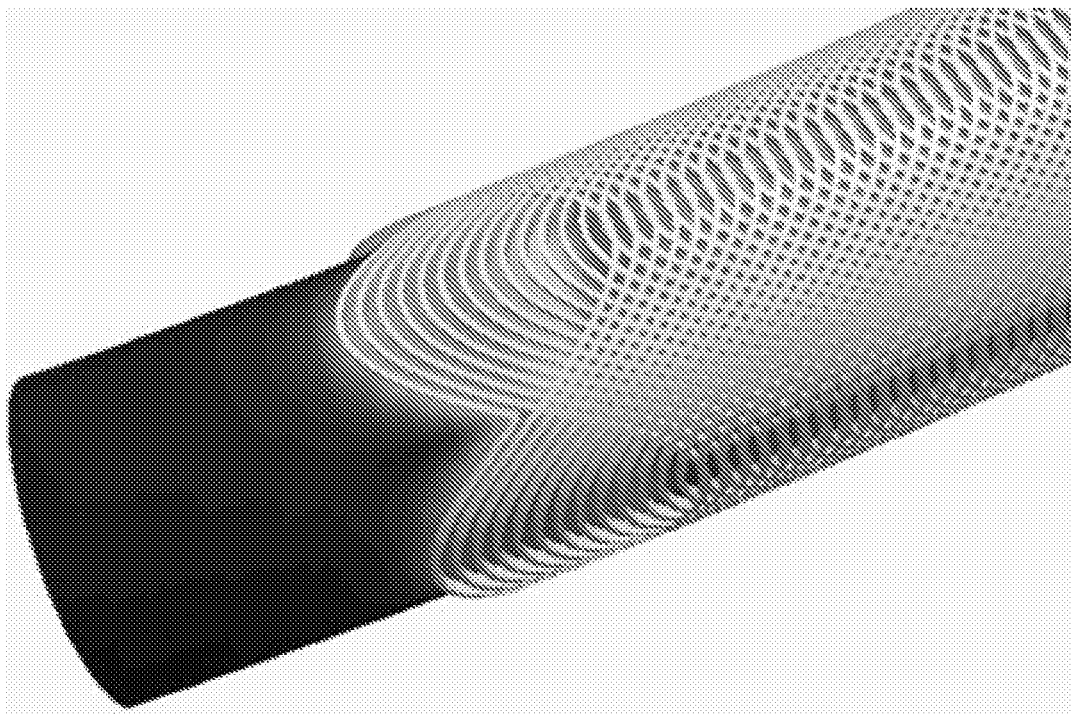
FIG. 2 illustrates examples of different multipole designs.
Figure 2:
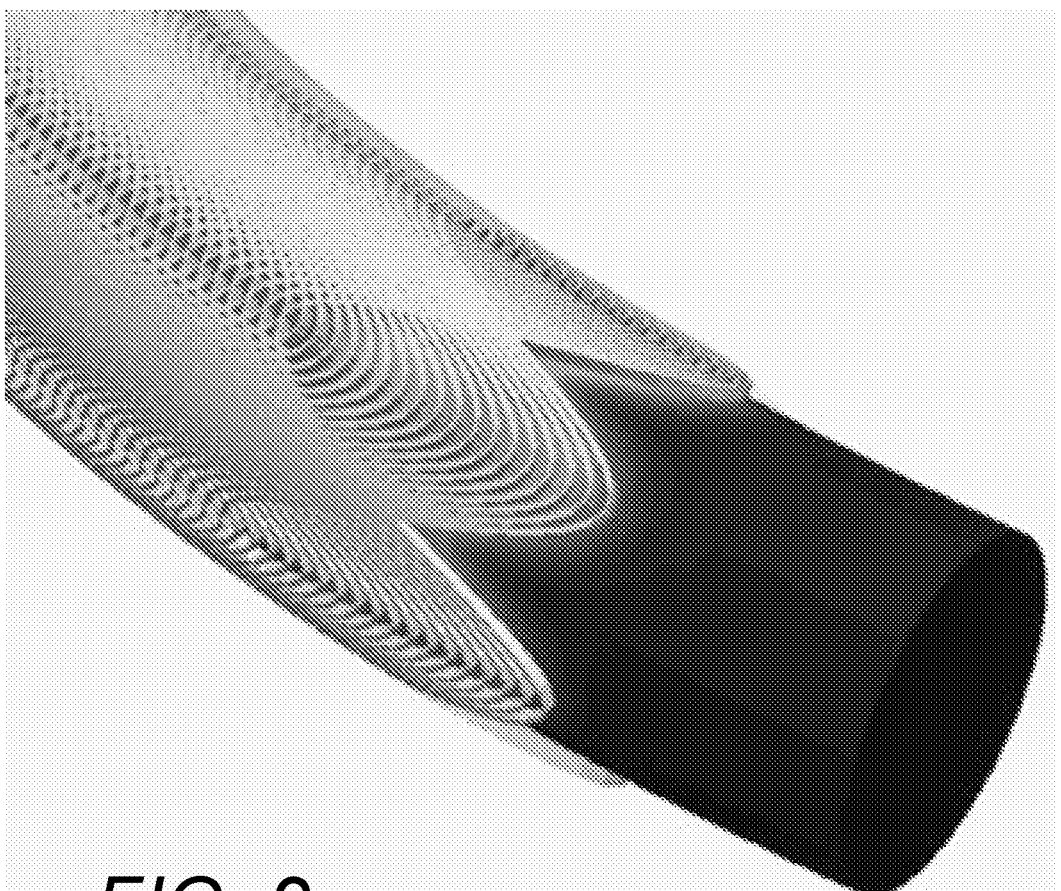

The superconducting gantry magnet 100 can have a canted-cosine theta (CCT) design based on the superposition of two solenoid windings on the inner layers 102a, 102b and two solenoid windings on the outer layers 104a, 104b that are oppositely skewed (canted) with respect to the bore axis. The respective combined current density of the two inner layers 102a, 102b and the two outer layers 104a, 104b can be cosine-theta-like (e.g., follows a $\cos(\theta)$ distribution for the two outer layers 104a, 104b and a $\cos(2\theta)$ distribution for the two inner layers 102a, 102b). The resulting magnetic field in the bore can be a quadrupole (for the inner layers 102a, 102b) and a dipole (for the outer layers 104a, 104b). This concept can be extended to higher order multipoles as well by changing the axial modulation of the windings. For example, sextupole, octupole, and other nth order multipole fields can be generated. These modulations can also be combined in the winding layers to produce a combined function coils that generate dipole, quadrupole, and sextupole fields in the bore to provide suitable or desirable functionality for the beam optics. In addition, the windings of each layer can include transition locations to change the azimuthal direction of the axial current, as described herein. This can be used to rapidly change the properties of the resulting magnetic fields provided by individual pairs of layers. Examples of different multipole designs are illustrated in FIG. 2, which are to be understood, in some embodiments, to include one or more transition locations where the direction of the windings around the bore changes thereby changing the azimuthal direction of the axial current.

The superconducting gantry magnet 100 can provide rapid changes in magnetic field properties by changing a direction of the windings while maintaining the pattern of the windings around the bore axis. By changing the direction of the windings at the transitions 107, the direction of the current around the bore can change direction. This can result in a rapid change in the magnetic field properties (e.g., by changing a direction of the quadrupole field in the bore axis).

The superconducting gantry magnet 100 can be formed around a portion of a torus. This can enable to superconducting gantry magnet 100 to bend particles along a beam path (e.g., to change the particle beam direction between about 60 degrees and 150 degrees, about 75 degrees, or about 90 degrees) while providing alternating focus and de-focus regions to provide a relatively small spot size and to provide a relatively large energy acceptance. The superconducting gantry magnet 100 can be configured to provide a relatively large aperture to allow upstream bending magnets to selectively direct the particle beam at a target or to selectively scan the particle beam over a target region.

By way of illustration, a circular aperture coil can provide a dipole field when the z-coordinate, z0, has the form $z(\theta)=c\theta+A^{*}\sin(n\theta)$ (e.g., where A can be considered as the amplitude of the sine function of the conductor path in the tilted turn). The case for n=1 describes the geometry of the canted-cosine-theta dipole and represents a sinusoidal modulation of the z-coordinate at a frequency of once per turn. Similarly, if the frequency of modulation is n=2, then the z-coordinate of the conductor path is $z(\theta)=c\theta+A^{*}\sin(2\theta)$. The resulting magnetic field of such a coil can produce a field with a component along the z-direction and a component that varies as 1/r in the x-y plane (e.g., a quadrupole). By combining two such coils, one inside the other, but with currents in the opposite direction, the solenoid fields can cancel and the quadrupole fields can add. The result is a quadrupole magnet. This concept can be extended to include higher multipole magnets; for instance, sextupoles and octupoles can be produced by using a frequency of the modulation function of n=3 and n=4 respectively. By changing the direction of the currents in respective quadrupole layers, and coordinating the changes in current direction so that they occur at substantially the same location along the z-axis, the direction of the quadrupole field can be configured to rapidly change. As described herein, this structure can be implemented on a cylinder (e.g., a focusing or shaping magnet) or a portion of a torus (e.g., a bending magnet).

The superconducting gantry magnet 100 can include low temperature superconductors (LTS) conductors or high temperature superconductors (HTS) conductors at low or elevated temperatures. Examples include the low-temperature superconductors (LTS) Nb3Sn and MgB2, and high-temperature superconductors (HTS) Bi2Sr2CaCu2O8+x and YBa2Cu3O7−δ. MgB2 may also be used due at least in part to its relatively high Tc (~18 K), isotropic properties, and potentially low cost.

The superconducting gantry magnet 100 structure places windings within ribs 116 and spars 118 that simultaneously intercept and guide Lorentz forces of each turn to reduce or prevent stress accumulation. With respect to other designs, the need for pre-stress in this concept is reduced by an order of magnitude, making it highly compatible with the use of strain sensitive superconductors, such as Nb3Sn or other high temperature superconductors (HTS), for example.

The superconducting gantry magnet 100 can provide an achromatic system that is designed to compensate for the divergence resulting from the finite energy spread in the beam which may be present in ion beams used in particle therapy. Typical spot beam scanning techniques utilize precise beam transport for accurate and reproducible dose delivery to the patient. However, when charged particles with slightly different energy traverse the same magnetic field, they experience different deflections. When particles with different energies travel on different trajectories they have different focal positions. In such a case, different parts of the beam spot may have different penetration ranges in the patient body, which would lead to loss of dose delivery precision—a main advantage of charged particle beams. This effect is similar to chromatic aberrations in optical systems. Accordingly, the superconducting gantry magnet 100 can advantageously provide achromatic properties of the gantry beam transport system to reduce or eliminate correlations between the beam energy and beam position and angle at the isocenter. This can effectively make the particle beam path less sensitive to energy variations of the incoming beam.

The superconducting gantry magnet 100 can advantageously provide the combination of properties including, for example, being configured to bend a high energy beam of ions by a large angle (e.g., about 90 degrees, or between about 60 and 150 degrees); having a large dipole field in order to bend the beam in a relatively small radius (e.g., between about 1 m and about 2 m); having a relatively large bore (e.g., on the order of about 30 centimeters diameter); and being achromatic. In some embodiments, the superconducting gantry magnet 100 can be configured to be achromatic over a range of momentum of at least ±6%, at least about ±10%, at least about ±25%, etc. In some embodiments, the superconducting gantry magnet 100 can be utilized in a gantry design for application of pencil beam scanning. The gantry implementing one or more of the superconducting gantry magnets 100 can have locally achromatic sections that provide a large momentum acceptance (e.g., $\Delta p/p \approx 25\%$). In some embodiments, the superconducting gantry magnet 100 can include a bore with a radius of about 15 cm which enables the application of pencil beam scanning in front of the magnet 100.

The superconducting gantry magnet 100 can be tailored to provide desired functionality. For example, for a straight dipole design, the tilt angle of the windings at the mid-plane can be chosen to tailor the integrated dipole field for a given physical length and bore diameter. For typical high field accelerator dipoles this angle can be between about 15 and about 30 degrees. A similar approach of simply canting the windings to produce a dipole, when applied in the curved geometry of a gantry magnet, can lead to the generation of a dipole field plus higher order multipole fields (e.g., quadrupole fields, sextupole fields, etc.). These effects can be accounted for in the design of a curved superconducting gantry magnet 100. For example, the dipole and quadrupole layers of a curved magnet 100 can be configured so that the axial modulation of the tilted path can be used to create a single higher order harmonic or other targeted higher order harmonics.

An example implementation provides a superconducting gantry magnet 100 that includes the mandrel, superconducting material wound around the mandrel, and aluminum support tube that weigh in total about 500 kg to about 750 kg. In the example implementation, the complete 90 degree bend magnet with internal support structure, cryogenic shielding, cryostat vacuum vessel, and cryocoolers can weigh on the order of about 5 to about 10 times less than typical systems (e.g., between about 2000 kg and about 6000 kg).

In an example implementation, the superconducting gantry magnet 100 includes four layers of single, continuous NbTi cable around a precision-machined, cylindrical, aluminum mandrel. A first layer, for example, has an inner diameter (clear-bore) of about 50.8 mm, an outer diameter of about 62.99 mm and is about 841.13 mm long. The mandrel includes about 80 conductor turns. At the mid-planes of the mandrels the ribs can be about 0.4 mm thick. A second layer, for example, has an inner diameter of about 63.5 mm, an outer diameter of about 76.2 mm, and is also about 841.13 mm long. This mandrel includes about 70 conductor turns. Between the mandrels, there is a 0.25 mm-0.38 mm, radial, inter-layer gap that includes a 1.27 mm-thick fiberglass-tape insulation wrap. Clearance may also be provided in the gap to allow the second layer mandrel to be slid over the wound and insulation-wrapped mandrel of the first layer. Additional layers can be added using mandrels of increasing size (e.g., increasing inner and outer diameters, but maintaining approximately the same length).

Example Method of Manufacture

Figure 3:
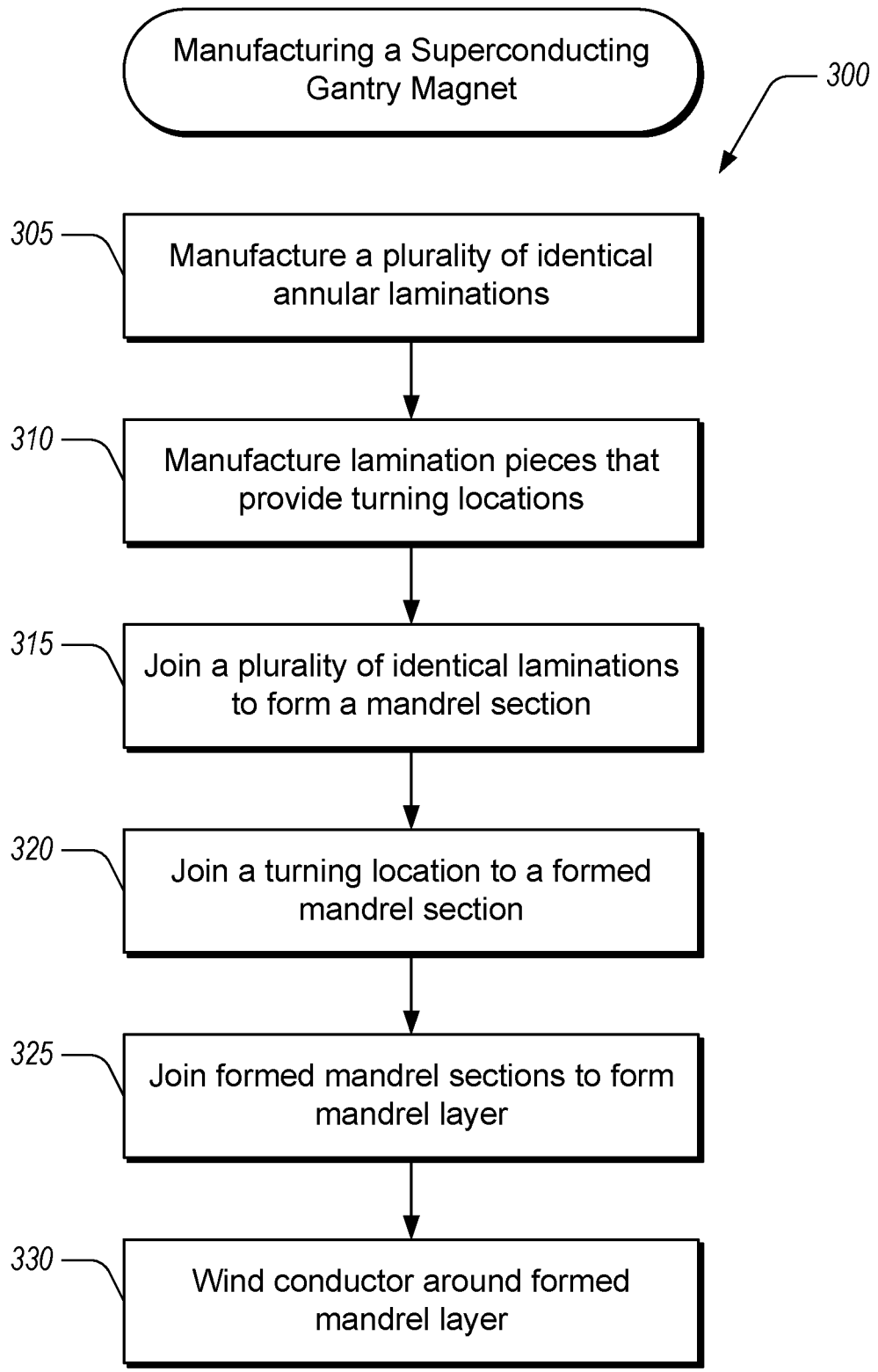
FIG. 3 illustrates a method for manufacturing a superconducting gantry magnet that includes two quadrupole layers with transition locations.

FIG. 3 illustrates a method 300 for manufacturing a superconducting gantry magnet that includes two quadrupole layers with transition locations, as described herein with reference to FIG. 1. The method 300 is described specifically for the quadrupole layers in a superconducting gantry magnet, but the disclosed manufacturing method can be extended or modified for dipole layers or other multipole layers. The method 300 includes manufacturing a mandrel which may affect the winding feasibility, cost, field quality, stress management, and eddy currents of the resulting superconducting gantry magnet. The method 300 can be used to produce a laminated mandrel that can be utilized for a 90 degree, superconducting, combined function magnet for use in a particle therapy gantry. Advantages of this design for the mandrel can include, for example, reducing eddy currents during field changes and simplifying manufacturing.

Figure 4:
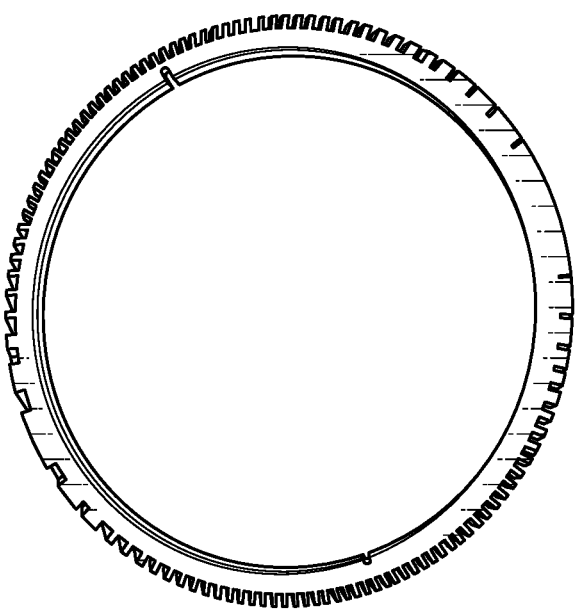
FIG. 4 illustrates an example laminate section used to manufacture a superconducting gantry magnet.
Figure 4:

In block 305, a plurality of identical annular laminations is manufactured to be joined together to from a mandrel for a layer of the superconducting gantry magnet. Symmetry in the winding path for the superconducting gantry magnet allows for the mandrel to be made out of stacked laminations along a cylinder or around the bend of a torus. For example, the winding path is symmetric in the sense that there exists a minimum annular slice of the mandrel that, when repeated, forms the winding path. An example laminated section is illustrated in FIG. 4. This minimum size represents a minimum section size of the mandrel, and the method 300 can include manufacturing a plurality of these minimum section sizes. In some embodiments, the method includes manufacturing a plurality of section sizes that are equivalent in design as an integer multiple of the minimum section size. For a bent superconducting gantry magnet, the minimum section sizes are tapered (e.g., wedge shaped) laminations. Due at least in part to the symmetric properties of the winding path, the entire information of the coil and structure, repeated as a single turn, can be contained in a single lamination of the minimum section size.

For example, the thickness of each lamination can be the length of an axial period of a turn. For longer sections of mandrel, the lengths can be in exact multiples of a turn period. For a curved magnet construction, the end planes of the laminations can be at a wedge-angle. For a straight-bored magnet, the end planes of the laminations can be parallel. When such identical laminations are stacked, the grooves can align to form a continuous groove for a conductor to lie in.

As a particular example, identical tapered laminations with thickness of a "pitch" ($\phi$ ¼ 0:51 where $\phi$ is the angle around the torus) repeat to form the mandrel. Just like in a solenoid where the conductor size determines the turn to turn pitch, the conductor and rib sizes in the superconducting gantry magnet in combination with the tilt angle determine the lamination and pitch length. Advantageously, this lamination approach increases manufacturing options, reduces power losses related to eddy currents, and simplifies numerical calculations. Because the symmetry of the winding path allows for the mandrel to be built piecewise out of small sections, this has the potential to simplify the production of the mandrel. For example, small identical laminations may be easier to fabricate than machining channels into a single large piece to form the mandrel. Similarly, this size difference may allow for more advantageous manufacturing techniques and mandrel materials to be used. Likewise, constructing the mandrel out of small laminations (that can be electrically isolated) reduces eddy currents produced within the mandrel as the magnet ramps to follow beam energy changes during treatment. For example, using symmetrical laminations of the minimum section size for a rectangular mandrel of similar size to a first layer of the gantry magnet reduces the eddy current loses by an approximate factor of 600.

In block 310, lamination pieces are manufactured that provide the turning locations for the superconducting gantry magnet. As described herein, the turning locations are locations where the winding changes direction around the mandrel to effectively change the direction of the current in the magnet, thereby changing the magnetic field properties within the bore. The turning location represents a conductor reversal. In designing the turning location, properties of the conductor are taken into account. For example, conductors have a minimum bend radius below which internal damage to the superconducting filaments may occur. In various implementations, the rib thickness, which varies with azimuthal angle, is largest at the pole and the turning location can be configured to be located at the pole, making use of the thick rib in that location. Placing the turning location at the pole region does not significantly impact the degrees of freedom available for optics design due at least in part to the large number of ribs providing a fine discretization of the longitudinal position selection for reversal, and the winding pitch angle provides further fine-tuning.

Figure 5:
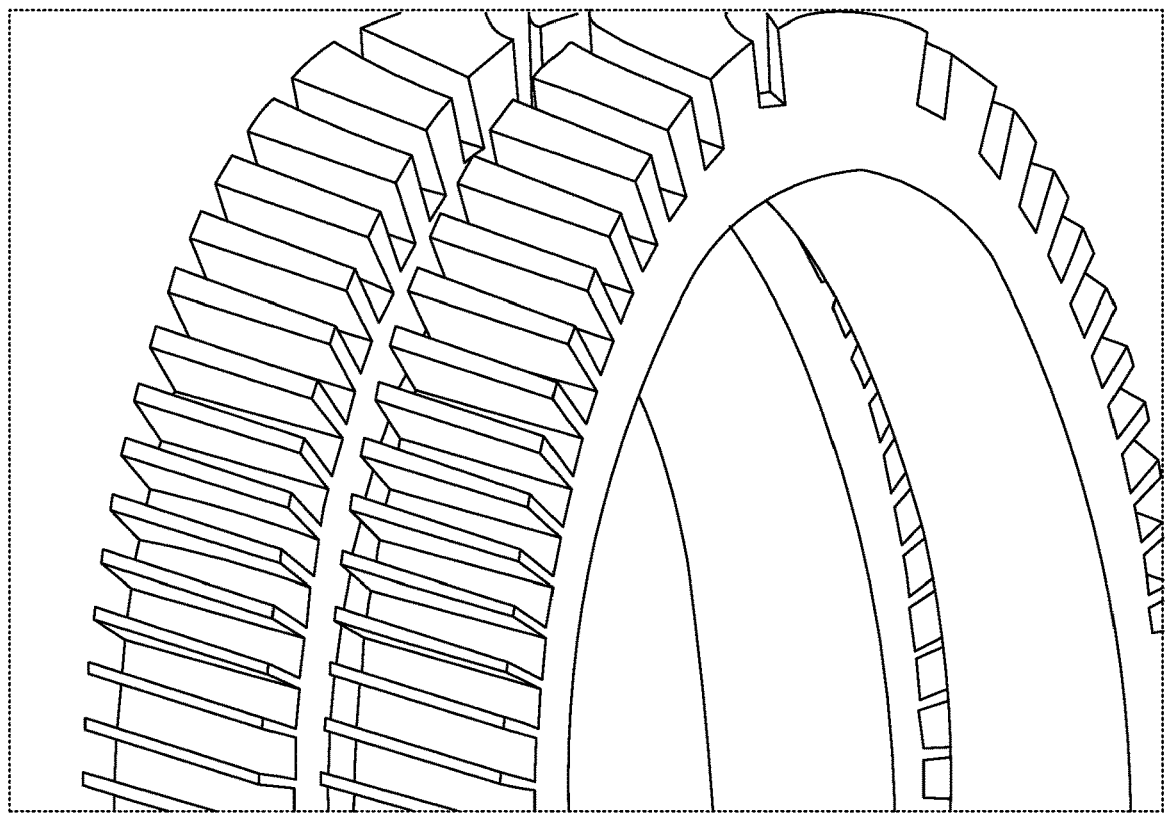
FIG. 5 illustrates an example of joined laminate sections forming a mandrel.
Figure 5:
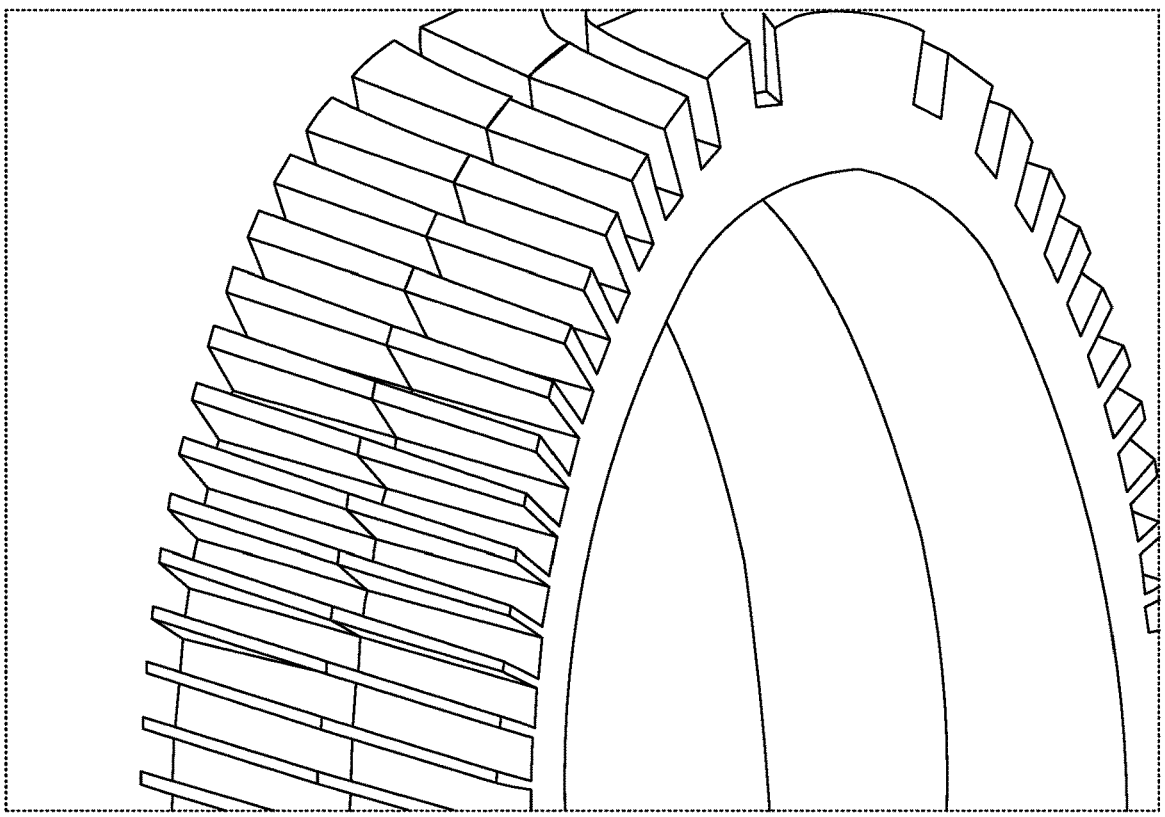

In block 315, a plurality of identical laminations are joined together to form individual sections of the mandrel of the superconducting gantry magnet. The identical laminations are joined so that the ribs and spars of the laminations align so that a continuous winding path is formed. A plurality of sections of the mandrel can be made in this fashion. Individual identical laminations can be joined together using adhesives. The individual laminations can include alignment features that facilitate alignment of the pieces when joining them together. For example, individual laminations can include alignment pins configured to align with one another when oriented so that the winding path forms a continuous path within the joined laminations. As used herein, a continuous path can refer to a path for a conductor that is not disjointed so that the conductor can be at least partially contained within the path when wound around the mandrel without breaking or cutting the conductor. Each conductor turn is supported in its own, individual channel formed by combining individual laminations. Separating each turn are the channel side-walls herein referred to as ribs. These ribs are part of a central mandrel tube herein referred to as the spar. An example of joined laminate sections forming a mandrel is illustrated in FIG. 5.

In block 320, a turning location lamination is joined to an individual section formed in block 315. The turning location lamination can be aligned with the individual section so that the ribs and spars of the section align with the ribs and spars of the turning location to form a continuous winding path with a turning location. The turning location lamination can be joined to the individual section using adhesives.

In block 325, sections with turning locations are joined to form an individual mandrel layer. By joining a plurality of the formed individual sections, the superconducting gantry magnet mandrel can provide a plurality of sections. In use, the plurality of sections can be used to provide alternating magnetic field properties, such as in an alternating gradient magnet, as described herein. For example, the mandrel formed using the method 300 can be for a quadrupole layer of a superconducting gantry magnet. The formed quadrupole layer can be configured to provide alternating focusing and de-focusing sections when combined with a complementary quadrupole layer nested within the formed quadrupole layer.

In block 330, a conductor is wound around the mandrel layer so that at least a portion of the conductor is contained within the formed continuous winding path with turning locations. In various implementations, Rutherford cables made of twisted superconducting strands may be used. Such cables may be advantageous to use in the method 300 due at least in part to their flexibility when bent. In some embodiments, a wide 23 strand cable may be used. In some embodiments, to reduce the effect of a hard bend on this cable the use of tilted channels, where the tilt orientation with respect to the bore varies azimuthally, may be used. This may allow the inner and outer edges of the cable to maintain a similar perimeter and may reduce conductor strain. In certain implementations, the conductor comprises NbTi rectangular, Rutherford cable made from eight 0.648 mm diameter SSC strands. The bare cable can measure about 2.718 mm wide by about 1.067 mm thick, with zero keystone angle. The cable can be insulated with braided-on S-Glass.

In some embodiments, winding the conductor includes inserting the mandrel layer over a spindle and set-up horizontally on a winding table that rotates around a vertical axis. The spindle/mandrel assembly can be driven to rotate 360-degrees around its horizontal axis. As the mandrel rotates, the table can swing so that the tensioned cable can be guided into the formed channels in the mandrel. As the mandrel continues to rotate and the cable reaches the opposite pole, the table can reverse and swing 180-degrees the other way.

The geometry of the conductor can be configured to enhance current density and hence the efficiency of field production while reducing the amount of winding materials. In certain implementations, it may be advantageous to have a cable conductor (e.g., a conductor composed of many single strands of superconducting wire an example of which is Rutherford cables where individual strands are in contact with each other and current flows in parallel). In various implementations, the conductors are configured to operate with a current of about 500 A or less. In some embodiments, the conductors can comprise individual strands that are cabled mechanically but electrically insulated from one another. In such embodiments, a joint box can be used to make the current flow serially through the strands. In various embodiments, it may be advantageous to maintain a positive curvature between the winding and the mandrel surface (e.g., the conductor during winding can pull into the mandrel to ease manufacture. The conductor can be NbTi, Nb3 Sn, MgB2 (or other HTS materials), or the like. In some embodiments, the diameter of the wire can be between about 1 mm and about 2 mm.

In some embodiments, after the coil assembly has been wound, it can be vacuum, epoxy-impregnated in a potting fixture.

In an example implementation, the mandrel has a bending radius of about 634 mm and clear bore of about 130 mm. The mandrel can be designed using sections and individual laminations can be joined to form these sections, which can then be assembled after manufacturing. One such section can be constructed out of about 50 single laminations, each lamination having a thickness of about 7 mm, for example. For this example implementation, the laminations could be manufactured having a thickness that is an integer multiple of the thickness of an individual minimum section size lamination (e.g., identical laminations can be about 14 mm thick, about 21 mm thick, about 28 mm thick, etc.). After being assembled, the mandrel can be wound with a single layer of eight-strand superconducting cable.

The method 300 can be suitable for a superconducting gantry magnet with a large bore diameter and a 90 degree bend. For example, the method 300 may be relatively easy to manufacture due at least in part to the conductor being in contact with the mandrel at all times during winding.

Figure 6:
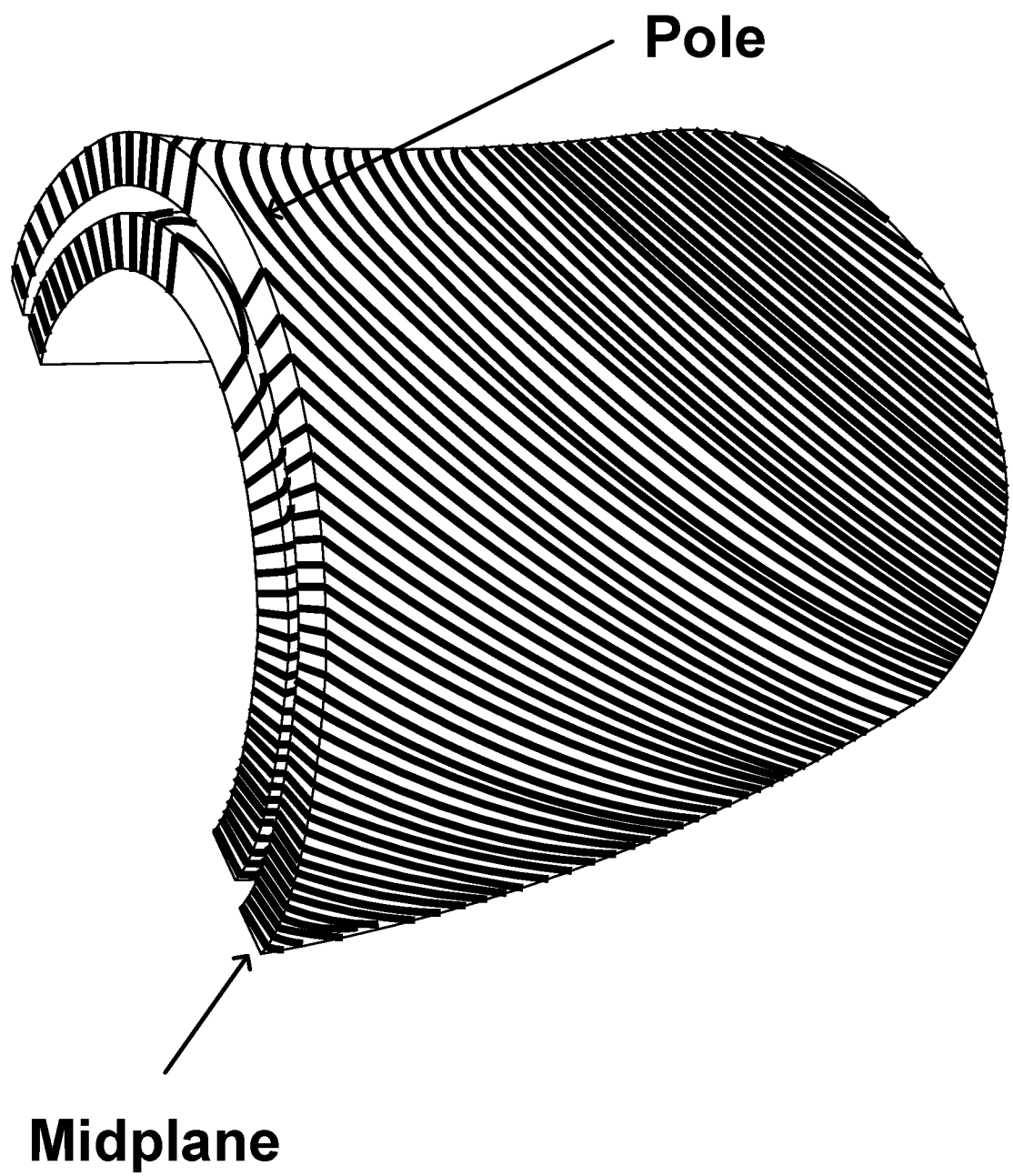
FIG. 6 illustrates an example mandrel that includes a variation in the channel wall thickness as the channel moves from the mid-plane to the pole.

The mandrel formed using the method 300 can advantageously include a variation in the channel wall thickness as the channel moves from the mid-plane to the pole, an example of which is illustrated in FIG. 6. The channels can be thin along the mid-planes (e.g., about 1.1 mm and about 0.7 mm on the torus outer and inner radii respectively), and thick at the poles (e.g., about 3.9 mm). The channel walls, or ribs, can act as intercepts to Lorentz forces that arise during use. The ribs can reduce or prevent stress accumulation between turns. The ribs can be formed as structural elements that are sufficiently thick to carry the load and to resist against bending of the channels. The intercepted Lorentz forces captured by the ribs can be guided towards the inner structural tubing to which the ribs are attached. An advantageous feature of the disclosed superconducting gantry magnet design is that the rib thickness varies similarly to the magnitude of the stress it intercepts. The radial stress on the cable varies in azimuth in a "cosine-theta" like manner, with large pressures near the mid-plane and little or no pressure near the poles. The transfer of forces to the mandrel can be compared to the way aerodynamic forces are distributed onto an airplane wing structure. For example, forces are carried from the wing skin (conductor cable) to the wing ribs (channel walls or ribs), which are directly attached to the main wing spar (central mandrel tube). The ribs are thicker at the pole regions and transfer the forces to the spar.

The longitudinal forces from each turn can be transferred to and accumulated in the mandrel spar. In certain implementations, the respective mandrel spars of a superconducting gantry magnet can be about 3.0 mm thick. The majority of the radial forces can be constrained by an external structure of a yoke subassembly. For example, at least a portion of the radial component of the Lorentz forces on a first layer can be intercepted by the spar of the mandrel of a second nested layer, and the radial force components on the second layer may be constrained by the external structure.

A superconducting gantry magnet can be formed using multiple layers. In certain implementations, an aluminum mandrel can be used with machined channels to guide and retain an NbTi Rutherford cable. For cable insulation, E2 fiberglass may be used for cable insulation and the coil can be impregnated. A preliminary coupling design between layers includes the impregnation of both layers to each other. A key and bladder assembly with an outer aluminum shell may be used for the magnet structure. In this design the iron yoke may be made of machined laminations roughly 20 mm in thickness that are tapered to match the curved geometry. The yoke may be loaded by an aluminum shell (using keys and bladders) to oppose operating radial Lorentz forces. This may provide sufficient pre-compression and reduce the possibility of conductor motion.

Example Compact Gantries for a Particle Therapy Facility

Figure 7:
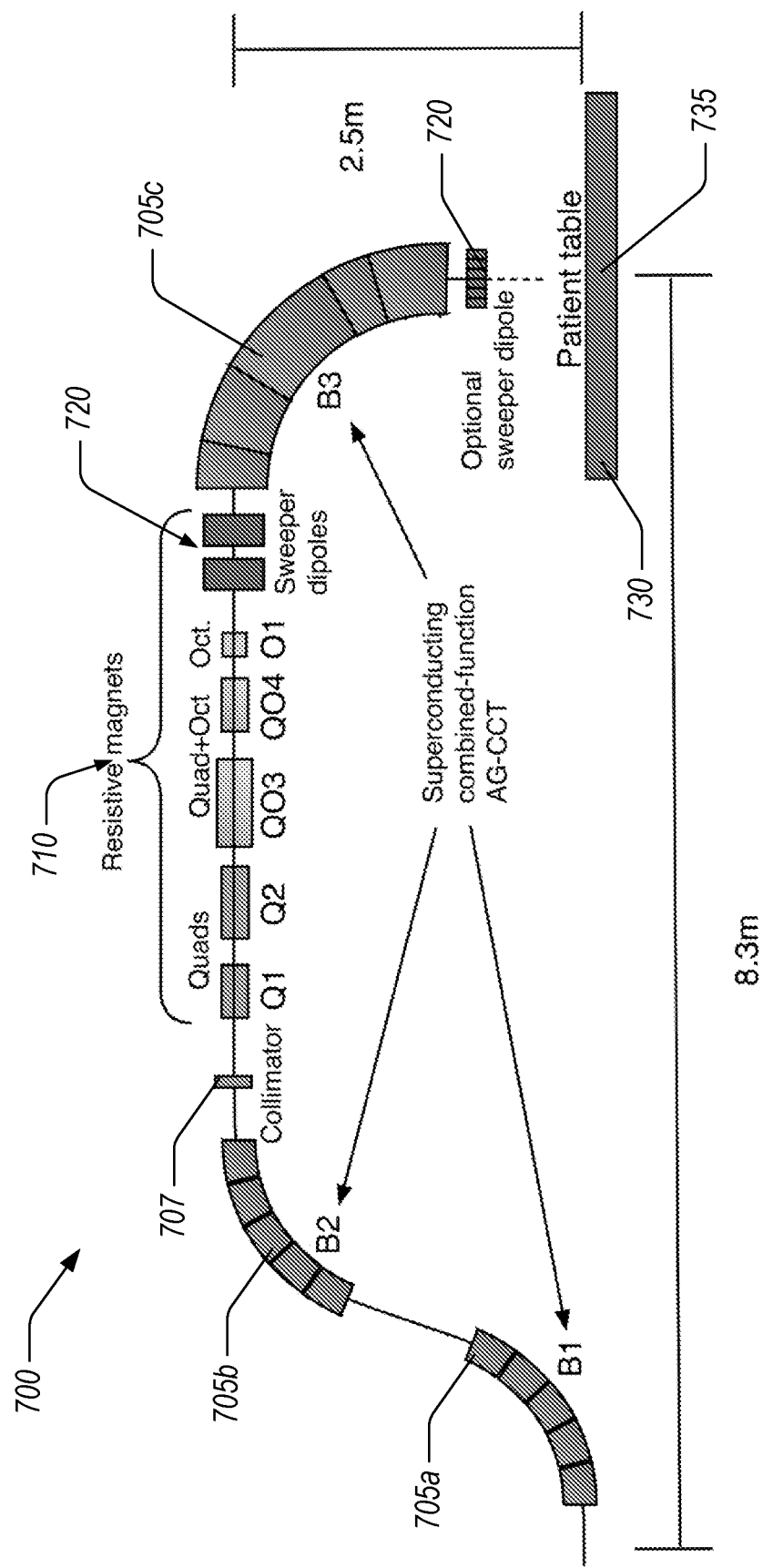
FIG. 7 illustrates an example gantry for a particle therapy facility, the gantry including two superconducting gantry magnets configured to redirect direct a beam path and a superconducting gantry magnet configured to provide a final 90-degree bend in the beam path.

FIG. 7 illustrates an example gantry 700 for a particle therapy facility, the gantry 700 including two superconducting gantry magnets 705a, 705b configured to redirect direct a beam path and a superconducting gantry magnet 705c configured to provide a final 90-degree bend in the beam path to direct particles to a target (e.g., a patient). Each of the superconducting gantry magnets 705a-705c comprise at least two dipole layers and at least two quadrupole layers, as described herein with reference to FIG. 1. The quadrupole layers are configured to alternative between focusing and de-focusing fields by changing the direction of conductor windings on the individual layers at transition locations.

The superconducting gantry magnets 705a, 705b are configured to bend a beam path by about 75 degrees and the superconducting gantry magnet 705c is configured to bend the beam path by about 90 degrees. The combination of the superconducting magnets 705a-705c can provide an achromatic system over a relatively large range of particle momenta. In some embodiments, the superconducting magnets 705a-705c can include sextupole and/or octupole layers to increase the range of momenta over which the system is achromatic.

The gantry 700 can be configured to provide pencil beam scanning over a range of depths without changing the fields of the superconducting magnets 705a-705c. This scanning can be accomplished with little or minimal distortion of the beam shape. Thus, the gantry 700 may be used to provide rapid 3-D scanning. In some embodiments, the superconducting magnet 705c providing the final 90 degree bend can weigh about an order of magnitude less than a typical 90 degree magnet (e.g., a non-superconducting magnet).

The gantry 700 can be configured to rotate a particle beam around a target 730 (e.g., a patient) to irradiate a tumor from different angles. Particle therapy gantries, such as the gantry 700, can be configured to scan the beam within the tumor volume in all three dimensions by modifying the transverse position and energy of the beam.

The gantry 700 includes additional room temperature magnets to accommodate fast energy changes before the gantry. For example, normal conducting magnets 710 (e.g., quadrupole magnets, octupole magnets, combination multipole magnets, etc.) can be placed in the beam line between the superconducting magnets 705b, 705c. The gantry 700 can also include scanning magnet 720 to provide transverse beam scanning.

In some embodiments, the gantry 700 can rotate ±180° or ±90° from the treatment room floor. A benefit of the gantry 700 is to allow geometrical flexibility of beam treatment angles with respect to a patient 730, who is usually lying on the treatment table 735.

A large acceptance is desirable to comply with the large emittance of particle beams (e.g., proton beams, carbon beams, etc.) that have been degraded to the targeted energy in a preceding beam transport system. A large acceptance of the beam transport system and the gantry can be configured to maintain beam intensity at the patient 730. In some embodiments, the beam spot at the isocenter can be relatively free of dispersion, the beam spot being substantially circular and Gaussian-like shaped with a (2σ) radius of about 4 mm to about 6 mm.

In some embodiments, the gantry 700 can be configured to rotate by at least an angle of about ±180° or about ±90° around the patient 730 with a distance of about 50 cm from the beamline exit (gantry nozzle) to the isocenter. An additional space downstream of the final bend magnet 705c may be occupied by beam diagnostics and dosimetry equipment. Accordingly it may be advantageous to maintain at least one meter distance between the end of the final bending magnet 705c and the isocenter.

The transverse scanning can be configured to cover a relatively large transverse area (called "scanning field") at the isocenter plane. The scanning field can be greater than about 20 cm×20 cm or greater than or equal to about 30 cm×40 cm. The scanning can be performed with fast normal conducting sweeper magnets to shift the pencil beam with a speed of a few cm/ms in the isocenter using reasonable magnetic fields (maximum deflection of up to 80 mrad). The round beam spot formed at the isocenter can be configured to remain substantially free from distortion by the scanning.

The scanning magnets 720 can be located upstream or downstream of the final bending magnet 705c. Downstream scanning may be advantageous because it may allow the final bending magnet 705c to have a relatively small aperture. For upstream scanning, the final bending magnet 705c can have a relatively large aperture to allow the scanned beam trajectories to pass through the magnet 705c. Upstream scanning may be advantageous to lower the skin dose that is obtained with parallel pencil beam displacements. Upstream scanning may also advantageously result in a gantry with a smaller gantry radius.

For the longitudinal or depth scanning by energy variation, it may be desirable to modulate the depth of the Bragg peak in water between about 4 cm and about 30 cm, corresponding to proton beam energies of about 70 MeV to about 220 MeV. Scanning may typically be performed in layers of about 5 mm depth (e.g., 5 mm depth corresponds to 1% change in beam momentum). To achieve a short treatment time, the corresponding energy step can be accomplished relatively quickly. For example, this energy step may be accomplished at about 100 ms. Accordingly, the gantry 700 can be configured to support a beam momentum change rate of about dp/dt=10%/s.

The gantry 700 begins at a coupling point (not shown) configured to separate the fixed beam line from the gantry 700. Following the coupling point the beam passes through two locally achromatic, 75° curved AG-CCT bend magnets 705a, 705b also labeled B1 and B2. After B2 a collimator 707 is placed at an image of the coupling point defining the beam size and divergence. Following the collimator 707 the beam is transported through a normal conducting quadrupole/octupole matching section 710 including five magnets. The first two, Q1 and Q2, are pure quadrupoles. The second two QO3 and QO4 are combined function quadrupole/octupole magnets. The final magnet O5 is a pure octupole. Following the matching section 710 are two sweeper magnets 720, first an out-of-plane and then an in-plane magnet used to scan the beam transversely over the field. Past the sweeper magnets 720, the beam passes through a larger aperture, locally achromatic, 90° curved AG-CCT bend magnet 705c. Finally the beam arrives at the isocenter 735. In some implementations, the length of the gantry can be about 8.3 m and the height of the gantry can be about 2.5 m. The height can be the distance between the isocenter 735 and the center of the beam pipe in the quadrupoles 710 and the length can be the distance between the gantry entrance and the isocenter 735.

The final bending magnet 705c can be relatively large aperture, be curved over a relatively large angle, produce combined function fields, and be capable of changing field relatively quickly to accommodate beam energy variation (e.g., between about 60 MeV and about 22 MeV for protons) during treatment scanning. In various implementations, the final bending magnet 705c can include a sextupole component for focusing and reducing or minimizing beam distortion. In such implementations, the respective pairs of layers can be powered so that within the bore the contributions of each layer to the solenoidal or axial field cancel and the transverse fields sum. The final bending magnet 705c can be configured to include conductor paths on the respective layers to generate a pure dipole field overlaid with quadrupole and sextupole terms. The desired combined function field can be tuned by tailoring the winding paths around the individual layers. In various example implementations, the final bending magnet 705c can have a bore diameter of about 130 mm, a dipole field of about 3.5 T, and a bending radius of about 634 mm (e.g., for protons up to about 220 MeV in energy). In certain implementations for a carbon beam, the final bending magnet 705c can be configured to be about two times the size of the magnet for protons and have about a 50% higher dipole field. In some embodiments, the quadrupole field can be about 3.17 T/m and the sextupole field can be about 1.84 T/m$^2$.

The isocentric gantries described herein can be configured to change the direction of a particle beam line by 90 degrees (e.g., change the direction of a horizontal beam line to a vertical beam line) or any other angle required incident on the patient. It should be understood that many combinations of angles can be used to design the beam transport that provides the desirable size and cost of the gantry. Various compact gantry envelopes are envisioned that may adjust diameter, overall height, length, and other dimensions as a result of beam line component selection and combinations as described herein.

The gantry 700 can be configured to image the beam from the collimator 707 to the isocenter 735 over a large range in momentum without changing the magnetic fields of the superconducting gantry magnets 705a, 705b. Placing the collimator 707 at the top of the gantry 700 rather than at the beginning of the gantry 700 may be advantageous for reducing the impact of the chromatic aberrations of the superconducting gantry magnets 705a, 705b on the momentum acceptance. In some embodiments, the magnets in the matching section 710 can have relatively large apertures and/or strong gradients and may be configured to change field as a function of beam momentum to maintain a targeted beam size.

The gantry 700 includes an achromatic system from the coupling point to the collimator 707 using two superconducting gantry magnets 705a, 705b that are locally achromatic AG-CCT magnets. The two superconducting gantry magnets 705a, 705b can be configured to image the beam from the beginning of the gantry 700 to the collimator 707. In some embodiments, the two superconducting gantry magnets 705a, 705b can be identical to each other, just bending in opposite directions.

Figure 8:
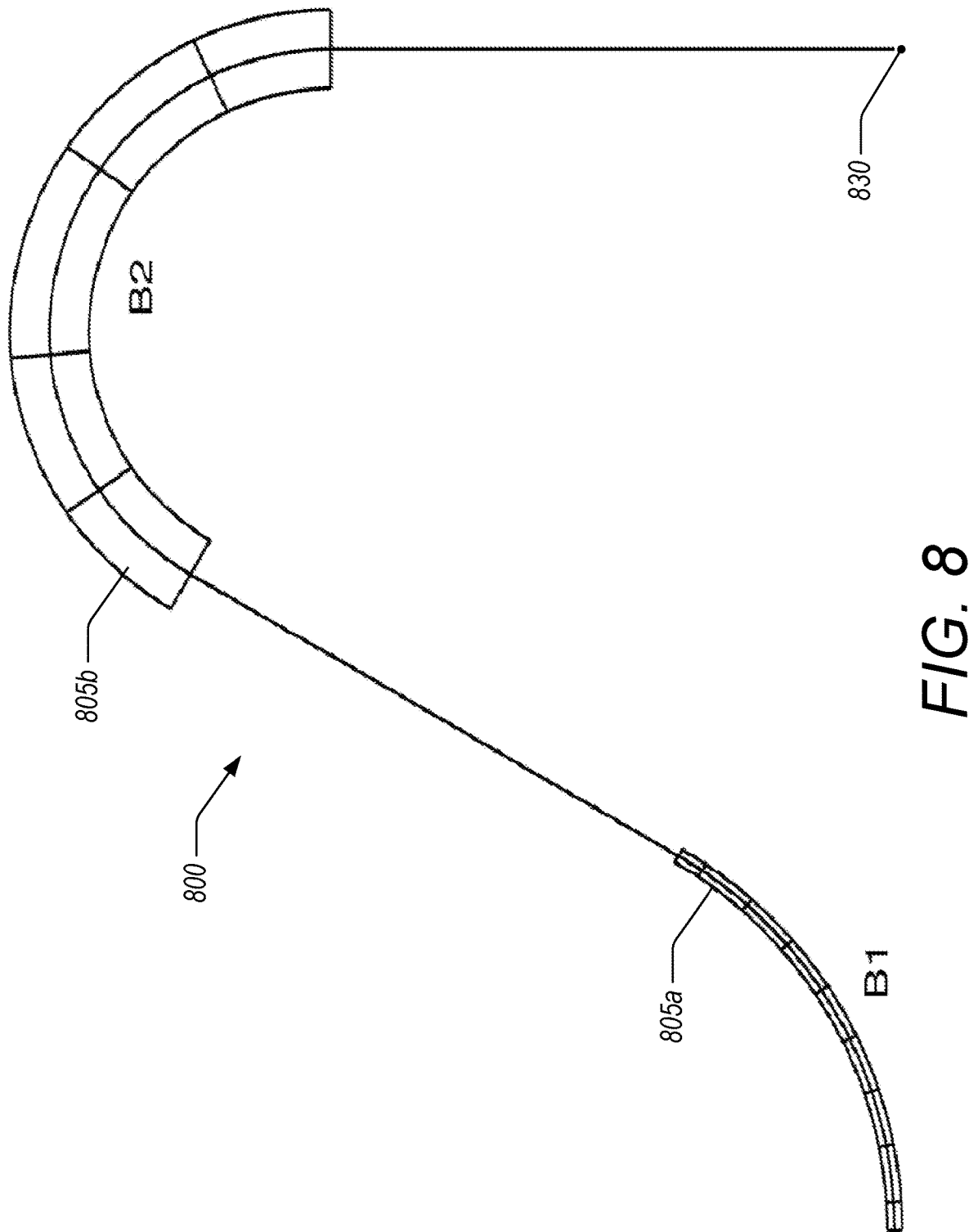
FIG. 8 illustrates an example gantry for a particle therapy facility, the gantry including a superconducting gantry magnet configured to redirect a beam path and a superconducting gantry magnet configured to direct the particle beam to a target.

FIG. 8 illustrates an example gantry 800 for a particle therapy facility, the gantry 800 including a superconducting gantry magnet 805a configured to redirect a beam path and a superconducting gantry magnet 805b configured to direct the particle beam to a target 830. The example gantry 800 is configured to exclude other resistive magnets typically configured to shape or otherwise adjust the characteristics of the beam, such as the matching section 710 of the example gantry 700 described herein with reference to FIG. 7. Using superconducting gantry magnets 805a, 805b that include sextupole and octupole layers can provide desired or suitable beam shaping functionality to reduce or eliminate the need for additional quadrupole or other similar resistive magnets in the gantry 800. Similarly, using superconducting gantry magnets 805a, 805b that include sextupole and octupole layers can provide an increase in the energy range over which the system is achromatic. For example, sextupole fields can be tailored to make a beam spot-size relatively independent of momentum (e.g., different energies focus at substantially the same position).

The gantry 800 can be configured to include relatively few magnets while maintaining the large momentum acceptance of the gantry 700. For example, the gantry includes two AG-CCT superconducting magnets 805a, 805b and the scanning magnets (not shown) that are located downstream of the magnet 805b. The superconducting magnets 805a, 805b each include 8 layers of coils that are configured to generate dipole, quadrupole, sextupole and octupole fields. The sextupole and octupole fields help to reduce or minimize aberrations generated by the strong quadrupole field and achieve large momentum acceptance without room temperature quadrupoles and octupoles present in the gantry 700.

The detailed parameters of the sections that contain superconducting magnets 805a, 805b (also referred to as B1 and B2) are listed in TABLES 1 and 2, respectively. Not listed are the total length and height (or radius) of the centroid of the beam, which are about 4.38 m and about 3.5 m, respectively, as well as the bore radius of B1 and B2, which are about 4 cm and about 13.5 cm, respectively. The peak field at the bore radius of B1 and B2 are about 5.48 T and about 4.27 T, respectively. The large bore radius of B2 may be determined by the expected maximum size of the beam assuming about 25% total momentum acceptance. It may be advantageous to have a smaller bore for B1, but this may increase the challenges associated with the windings for that magnet. As illustrated, there are four transition locations (resulting in five alternating fields: FDFDF), but it is to be understood that the number of transition locations can be different to provide additional or fewer field regions. For example, there can be at least 7 regions, at least 8 regions, at least 9 regions, etc.

TABLE 1

Parameters of the section that contains B1.

| Type | L/Ang (m/deg) | R (m) | B0 (T) | B1 (T/m) | B2 (T/m$^2$) | B3 (T/m$^3$) |
|---|---|---|---|---|---|---|
| Drift | 0 | — | — | — | — | — |
| Bend | 3.736 | 1.920 | 1.075 | 80.02 | 438.6 | −839.8 |
| Bend | 7.528 | 1.920 | 1.075 | −80.02 | −683.9 | −839.8 |
| Bend | 7.472 | 1.920 | 1.075 | 80.02 | 438.6 | −839.8 |
| Bend | 7.528 | 1.920 | 1.075 | −80.02 | −683.9 | −839.8 |
| Bend | 7.472 | 1.920 | 1.075 | 80.02 | 438.6 | −839.8 |
| Bend | 7.528 | 1.920 | 1.075 | −80.02 | −683.9 | −839.8 |

TABLE 2

Parameters of the section that contains B2

| Type | L/Ang (m/deg) | R (m) | B0 (T) | B1 (T/m) | B2 (T/m$^2$) | B3 (T/m$^3$) |
|---|---|---|---|---|---|---|
| Drift | 2.500 | — | — | — | — | — |
| Bend | 13.44 | 1.250 | 1.622 | 8.653 | −1.975 | 1.119 |
| Bend | 10.04 | 1.250 | 1.622 | −8.653 | −1.975 | −1.119 |
| Bend | 13.05 | 1.250 | 1.622 | 8.653 | −1.975 | 1.119 |
| Bend | 10.04 | 1.250 | 1.622 | −8.653 | −1.975 | −1.119 |
| Bend | 13.44 | 1.250 | 1.622 | 8.653 | −1.975 | 1.119 |
| Drift | 2.500 | — | — | — | — | — |

Figure 9:
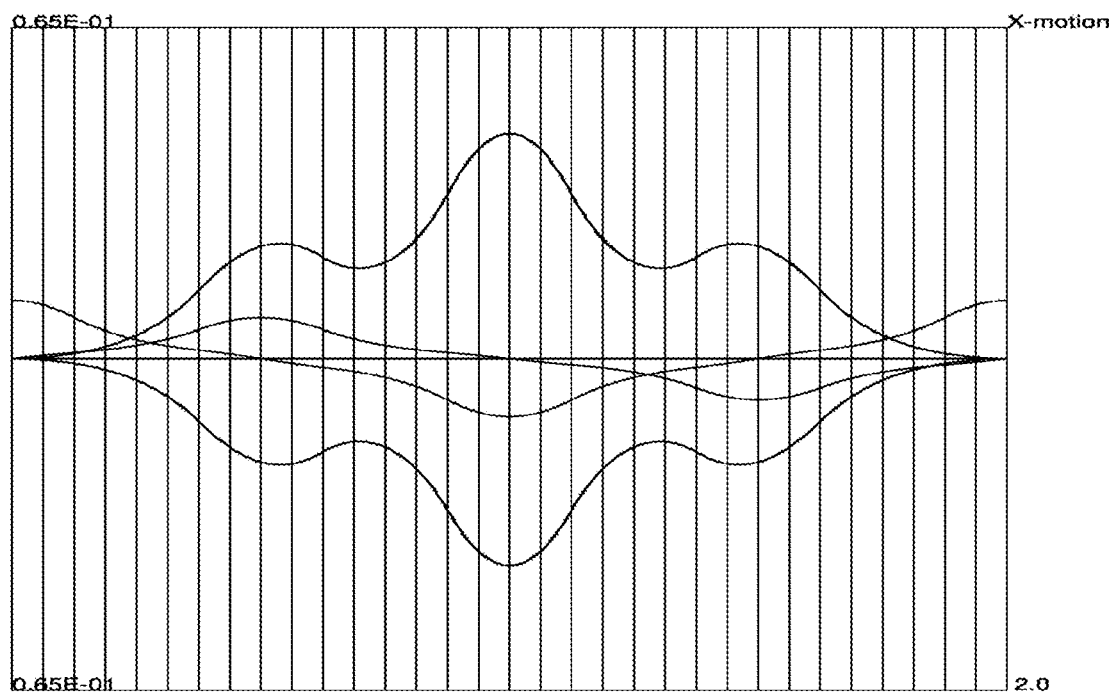
FIGS. 9 and 10 illustrates principle rays going through example superconducting magnets in a gantry, the superconducting magnets having at least eight layers comprising two dipole layers, two left-right quadrupole layers, two left-right sextupole layers, and two left-right octupole layers.
Figure 9:
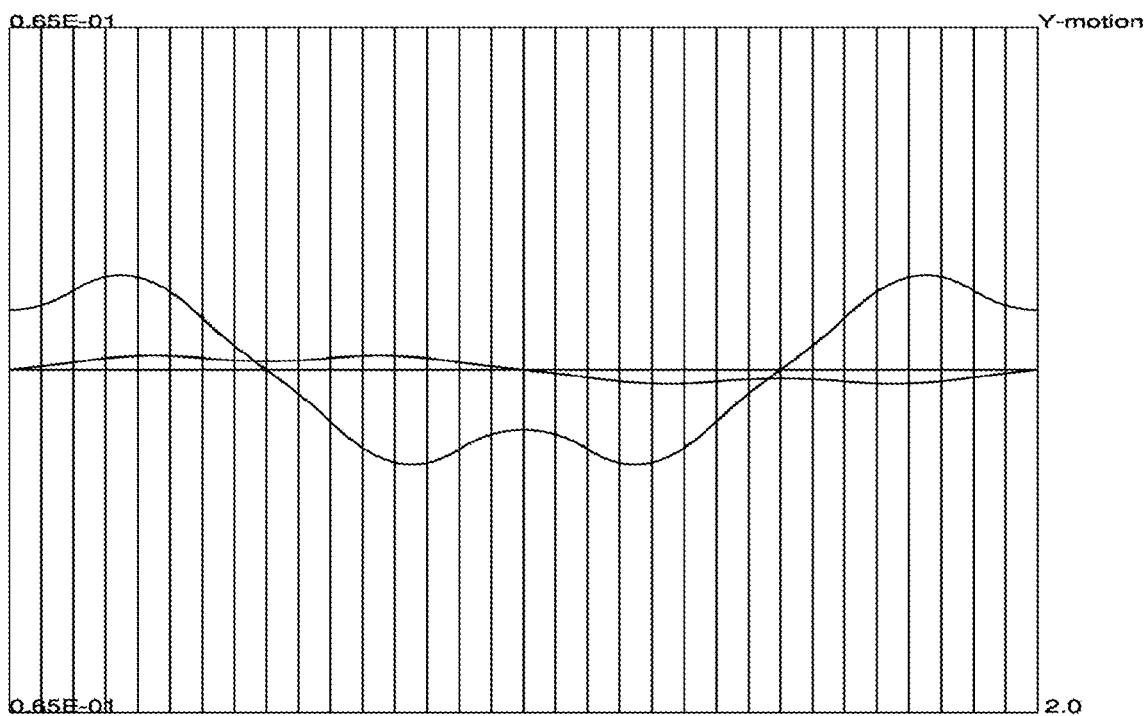
Figure 10:
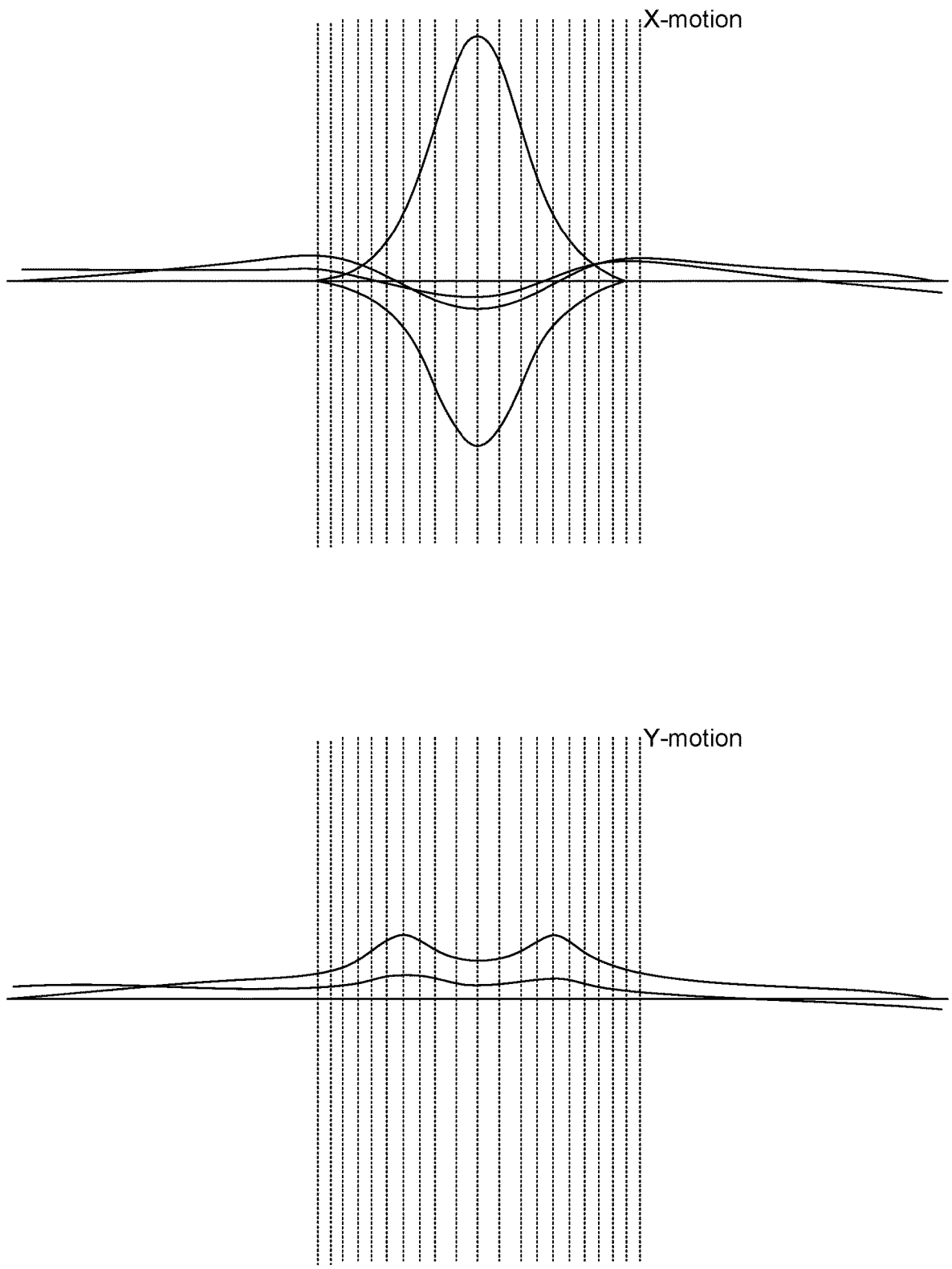
Figure 11A:
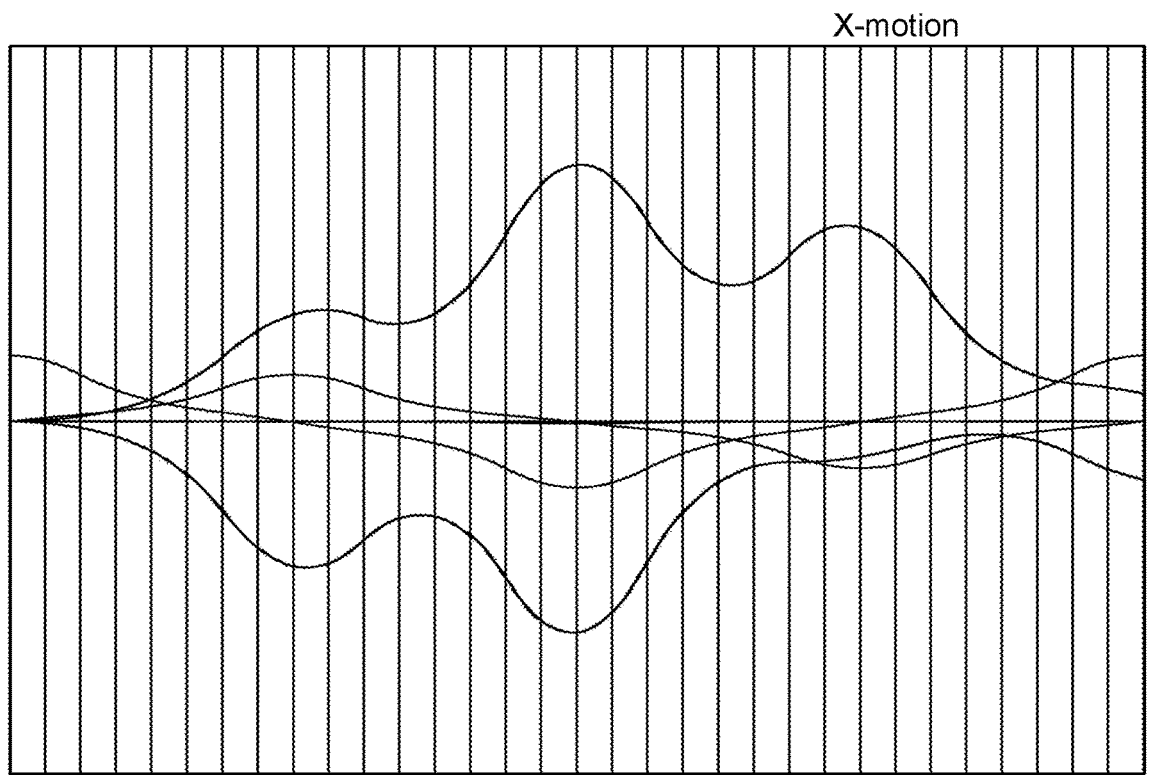
FIGS. 11A-C and 12 illustrate the effects of the sextupole and octupole fields on the principle rays going through example superconducting magnets in a gantry.
Figure 11A:
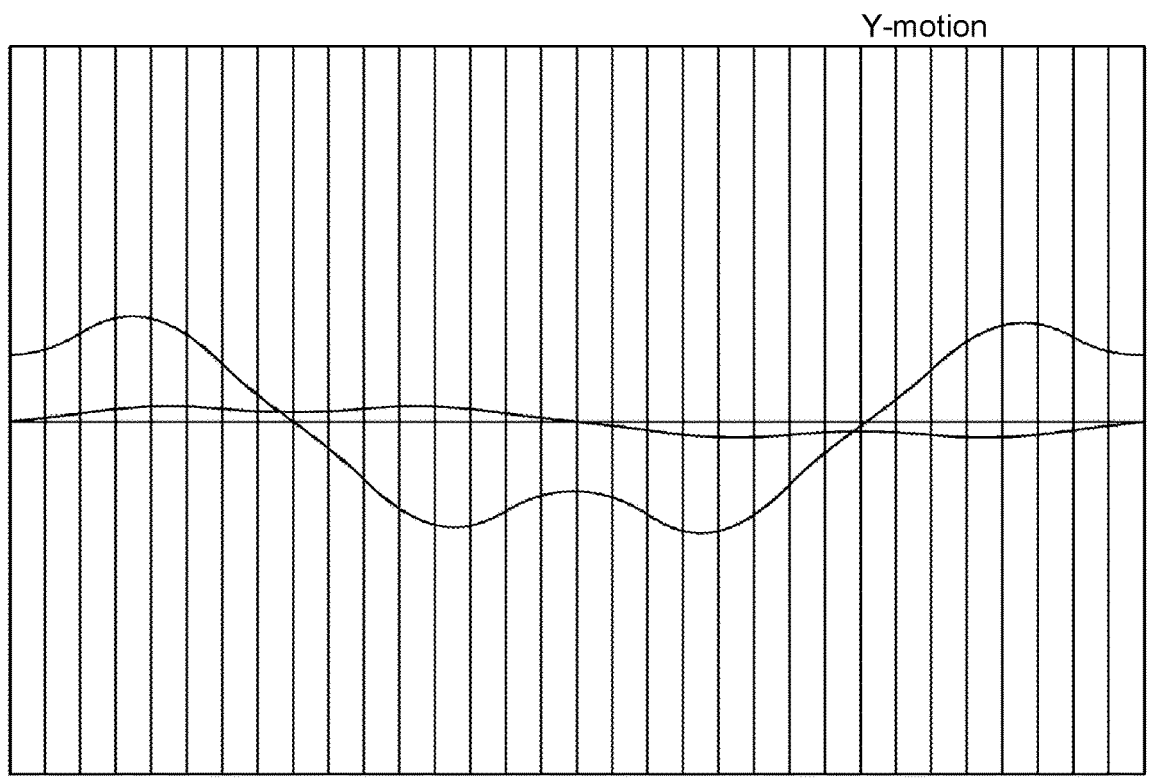
Figure 11B:
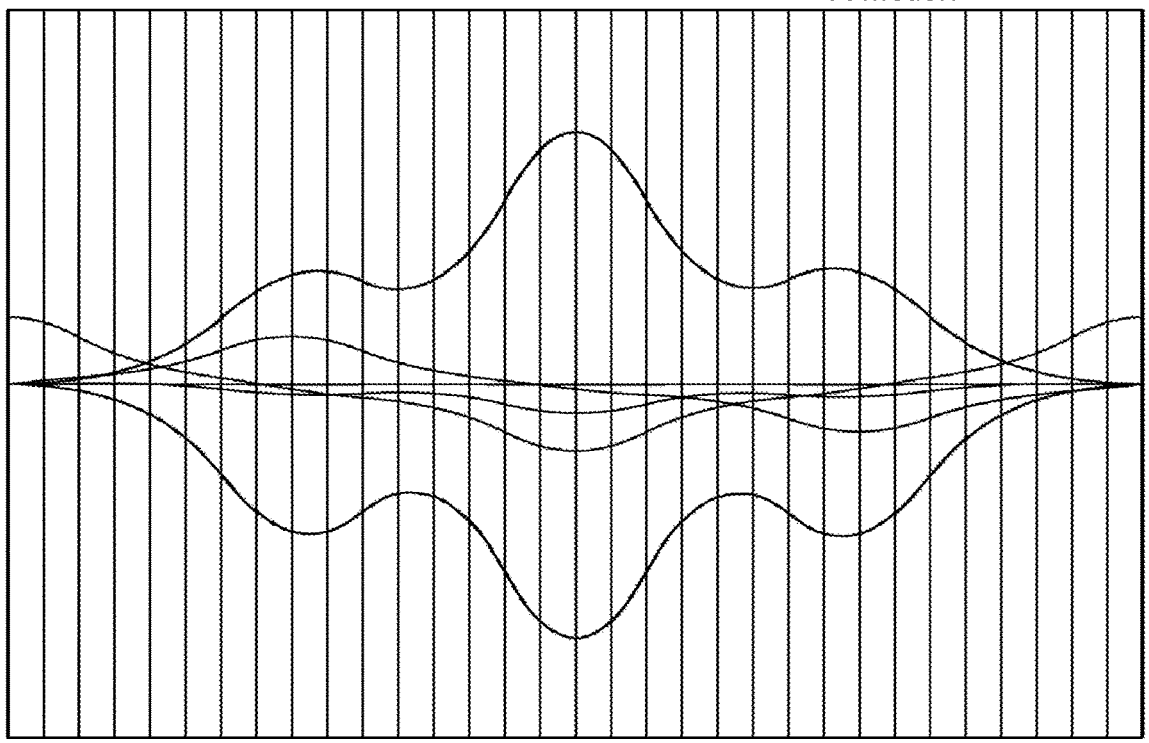
Figure 11B:
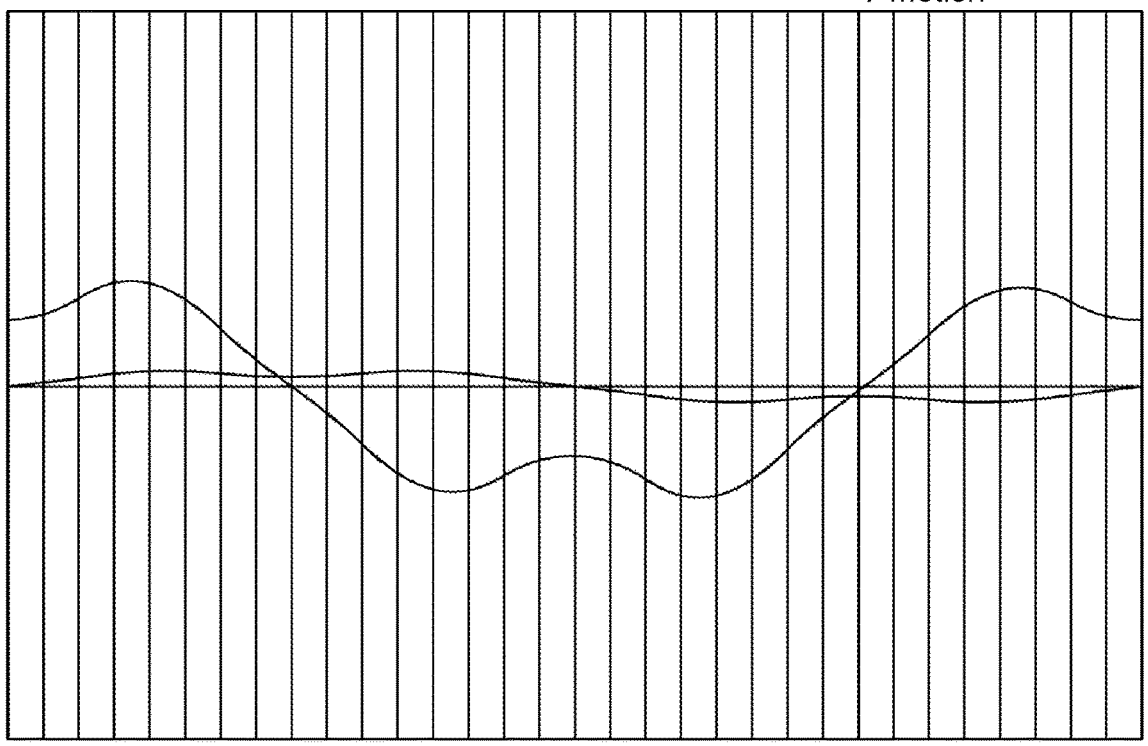
Figure 11C:
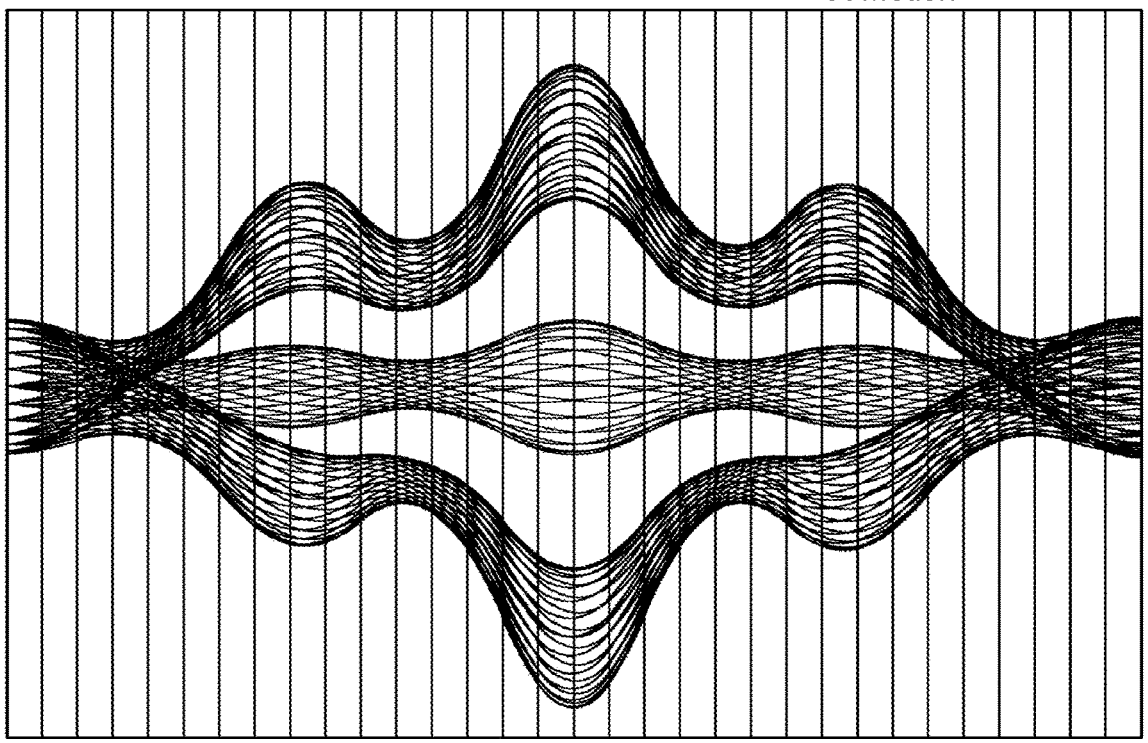
Figure 11C:
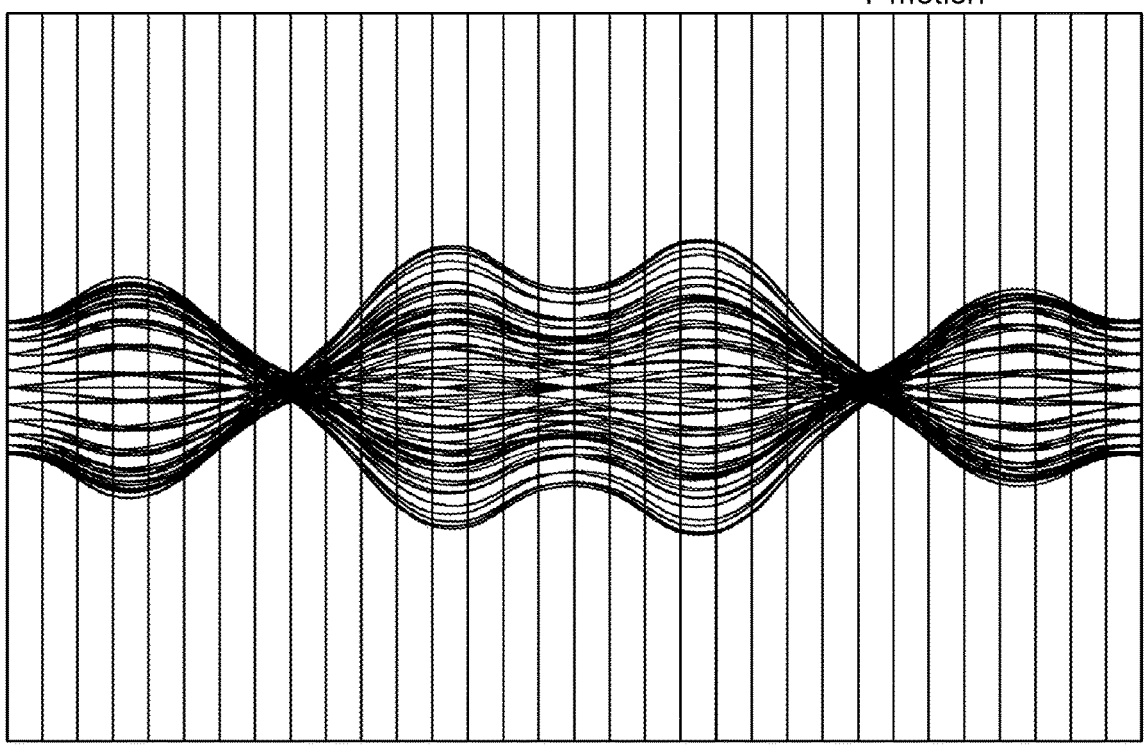
Figure 12:
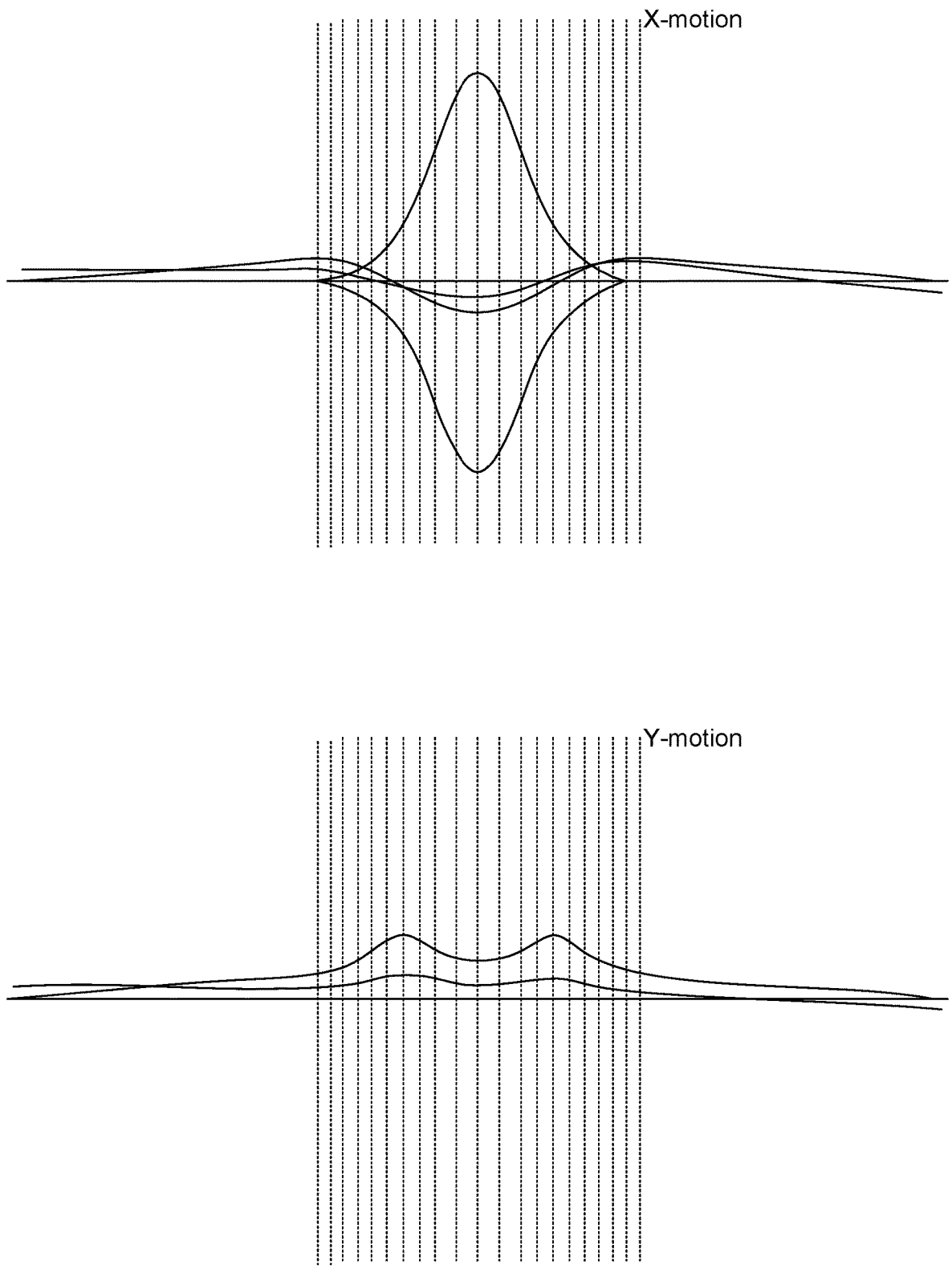

FIGS. 9 and 10 illustrate principle rays going through B1 and B2, respectively. In some embodiments, an energy degrader or a collimator can be placed after B1. This may result in decoupling of the two sections, reducing or minimizing the effect of the aberrations. FIG. 9 illustrates principle rays going through B1 where initial conditions are: x0=y0=5.7 mm, px0/p0=py0/p0=5.263 mrad and dp/p=−10.5% and 14.5%. FIG. 10 illustrates principle rays going through B2 where initial conditions are x0=y0=5.7 mm, px0/p0=py0/p0=5.263 mrad and dp/p=−10.5% and 14.5%. To produce the plots in FIGS. 9 and 10, the beam is tracked using a first order map. This can result in the plots not including aberrations that would be present using higher order tracking. FIGS. 11A-C and 12, on the other hand, include higher order effects to produce the plots. In addition, the plots in FIGS. 11B, 11C and 12 are produced when the magnets include sextupole and octupole fields. FIG. 11A is produced when the magnets do not include sextupole and octupole fields. FIG. 11C is produced by tracing multiple particles through the magnets and illustrates how these rays converge relatively independent of momentum. The presence of the sextupole and octupole fields results in the principle rays ending at roughly the same position when aberrations are taken into account (e.g., the plots in FIGS. 11B, 11C and 12) compared to when they are not taken into account (e.g. the plots in FIGS. 9 and 10).

Example Performance of Superconducting Gantry Magnets

Simulations can be used to analyze the magnetic fields of the disclosed superconducting gantry magnets. For example, optical and dynamics performance can be analyzed using the 3D field derived from the actual windings of disclosed AG-CCT magnets (e.g., the superconducting gantry magnet 100 described herein with reference to FIG. 1) simulated with the full equations of motion to determine beam properties. The results show that with appropriate higher order correction, a 3D volume (large transverse scanning field and up to Δp/p≈25%) can be scanned with little beam shape distortion without changing the magnetic field of the AG-CCT magnet. Thus, the disclosed magnets can be used to provide fast 3D scanning without also requiring fast field ramping of the superconducting magnets—addressing a technical risk (e.g., quench) associated with implementing superconducting technology in medical gantries.

For the superconducting gantry magnets, the simulation of the dipole and quadrupole layers include the quadrupole layers configured to provide alternating FDFDF functionality, referred to herein as an AG-CCT magnet (alternating gradient, canted-cosine-theta magnet). At each position in the magnets, the 3-D fields are calculated using Biot-Savart Law derived from about 200,000 line current segments of the 2 dipole and 2 quadrupole coils.

Figure 13:
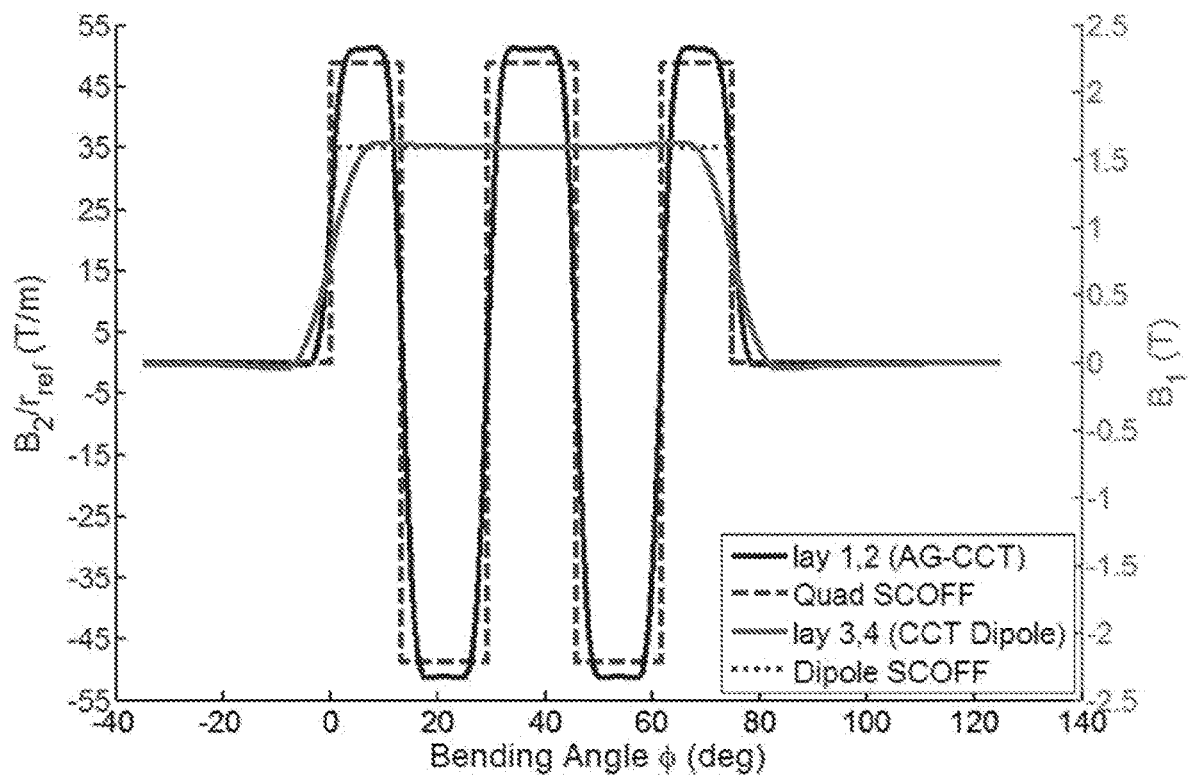
FIGS. 13 and 14 illustrate simulated magnetic field strengths, comparing the results to SCOFF model fields.
Figure 14:
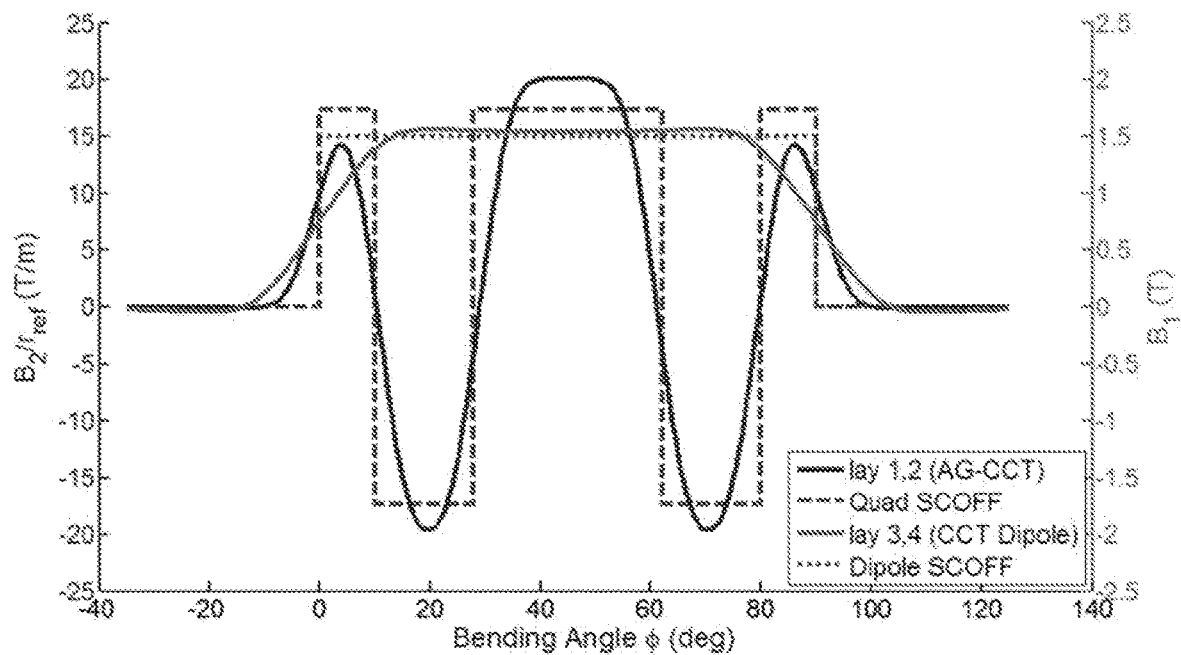

The resulting fields are shown in FIGS. 13 and 14 and can be compared with SCOFF model fields used (dotted lines) in the same figures. As illustrated in the figures, the fringes and transitions between the various F and D sections are smooth and well behaved. The agreement between the real fields and SCOFF fields is closer in a 75 degree AG-CCT than in the 90 AG-CCT (e.g., the magnets 705a, 705b described herein with reference to FIG. 7). This may be due at least in part to the 75° magnet having a smaller aperture than the 90° degree magnet. The magnitude of the gradient for each of the FDFDF quadrupole sections is the same—only the sign changes. Since the magnet is symmetric and the total bending angle is fixed there are just three parameters (e.g., the magnitude of the gradient, the locations of the transition from the first F to the first D, and the transition from the first D to the second F). These three parameters can be adjusted to satisfy the achromatic condition and to provide good transport properties.

Compared to the SCOFF model, the full field AG-CCT fields change the SAD slightly (the in-plane SAD is 2.8% longer and the out-of-plane SAD is 2.3% shorter). Also for the full fields, the in-plane sweeper response at the isocenter is 10% stronger and the out-of-plane is 7.4% weaker. As a result, the quadrupoles may be adjusted to compensate for the difference.

Simulation results show that the magnets B1 and B2 (e.g., the magnets 705a, 705b described herein with reference to FIG. 7) in the present form can transport the beam with little or no significant blurring of the image at the collimator. In certain implementations, sextupole coils can be included in the magnets B1 and B2 to correct for second order dispersion and chromaticity and, in some embodiments, octupole coils can be added to correct the third order geometrical aberrations generated by the sextupoles. In certain implementations, simulations demonstrate that with octupoles, third order aberrations between the collimator and the isocenter can be nearly negated for a range of momentum of about ±20%. In some embodiments, a total range of $\Delta p/p=25\%$ can be configured to cover an equivalent treatment depth range of about 4 cm to about 30 cm. In certain implementations, three different AG-CCT magnet settings can be used to cover this treatment depth. In certain implementations, a gantry system employing one or more of the disclosed AG-CCT magnets can be configured to scan over a relatively large transverse field (e.g., on the order of about 23 cm×about 14 cm) and over a momentum range of about ±25% with little or minimal beam distortion without changing the fields of the superconducting AG-CCT magnets. This can enable a gantry design using locally achromatic AG-CCT superconducting magnetic sections.

Terminology

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A superconducting gantry magnet comprising:
    a pair of quadrupole layers configured to provide an alternating quadrupole field in a bore of the superconducting gantry magnet, each quadrupole layer comprising:
        a mandrel comprising ribs forming a helical conductor channel comprising an undulating canted pattern around a bore axis of the superconducting gantry magnet;
        a plurality of transition locations formed by the conductor channel configured to change a direction of winding around the mandrel while maintaining the same undulating canted pattern; and
        a superconductor cable wound around the mandrel within the conductor channel such that each quadrupole layer includes at least two sections of the superconductor cable having the same cant and opposite winding directions about the bore axis;
    a pair of dipole layers configured to provide a dipole field in the bore of the superconducting gantry magnet, each dipole layer comprising:
        a mandrel comprising ribs forming a helical conductor channel comprising a canted pattern around a bore axis of the superconducting gantry magnet; and
        a superconductor wire or cable wound around the mandrel within the conductor channel,
    wherein the respective mandrels are configured to nest within one another around the bore axis, and
    wherein the quadrupole layers are nested inside the dipole layers and have outer diameters smaller than inner diameters of the dipole layers, or the dipole layers are nested inside the quadrupole layers and have outer diameters smaller than inner diameters of the quadrupole layers.

2. The superconducting gantry magnet of claim 1 further comprising a quadrupole power supply configured to provide electrical power to the superconductor wires or cables of the quadrupole layers and a dipole power supply configured to provide electrical power to the superconducting wires or cables of the dipole layers.

3. The superconducting gantry magnet of claim 1, wherein the alternating quadrupole field is configured to alternate between focusing and de-focusing sections.

4. The superconducting gantry magnet of claim 3, wherein the alternating quadrupole field includes at least three alternating sections.

5. The superconducting gantry magnet of claim 3, wherein the alternating quadrupole field includes at least five alternating sections.

6. The superconducting gantry magnet of claim 1, wherein the dipole field has a strength that is at least about 2 T and the quadrupole field has a strength that is at least about 20 T/m within the bore.

7. The superconducting gantry magnet of claim 1, wherein the superconducting gantry magnet is substantially achromatic over a range of energies of about ±20%.

8. The superconducting gantry magnet of claim 1 further comprising a pair of sextupole layers configured to provide an alternating sextupole field in the bore of the superconducting gantry magnet, each sextupole layer comprising:
- a mandrel comprising ribs forming a helical conductor channel comprising an undulating canted pattern around a bore axis of the superconducting gantry magnet;
- a plurality of transition locations formed by the conductor channel configured to change a direction of the winding around the mandrel while maintaining the same undulating canted pattern; and
- a superconductor wire or cable wound around the mandrel within the conductor channel.

9. The superconducting gantry magnet of claim 1, wherein the respective mandrels form a portion of a torus.

* * * * *